(12) United States Patent
Lerner et al.

(10) Patent No.: US 11,915,833 B2
(45) Date of Patent: Feb. 27, 2024

(54) INTEGRATED SYSTEM AND METHOD FOR PERSONALIZED STRATIFICATION AND PREDICTION OF NEURODEGENERATIVE DISEASE

(71) Applicant: B. G. Negev Technologies and Applications Ltd., at Ben-Gurion University, Beer-Sheva (IL)

(72) Inventors: Boaz Lerner, Mazkeret Batia (IL); Jonathan Gordon, Cambridge (GB); Aviv Nahon, Tel Aviv (IL)

(73) Assignee: B. G. Negev Technologies and Applications Ltd., at Ben-Gurion University, Beer-Sheva (IL)

( * ) Notice: Subject to any disclaimer, the term of this patent is extended or adjusted under 35 U.S.C. 154(b) by 292 days.

(21) Appl. No.: 17/311,491

(22) PCT Filed: Dec. 6, 2018

(86) PCT No.: PCT/IL2018/051340
§ 371 (c)(1),
(2) Date: Jun. 7, 2021

(87) PCT Pub. No.: WO2020/115730
PCT Pub. Date: Jun. 11, 2020

(65) Prior Publication Data
US 2022/0093272 A1 Mar. 24, 2022

(51) Int. Cl.
*G16H 50/70* (2018.01)
*G06N 20/20* (2019.01)
*G16H 50/50* (2018.01)

(52) U.S. Cl.
CPC .............. *G16H 50/70* (2018.01); *G06N 20/20* (2019.01); *G16H 50/50* (2018.01)

(58) Field of Classification Search
CPC ......... G16H 10/00–80/00; G06N 3/00–99/007
See application file for complete search history.

(56) References Cited

U.S. PATENT DOCUMENTS 10,438,695 B1 * 10/2019 Wittenstein ............ G16H 50/20
2004/0172225 A1 * 9/2004 Hochberg ............... G16H 50/30
703/2

(Continued)

FOREIGN PATENT DOCUMENTS

WO 2014163444 A1 10/2014
WO WO-2018172540 A1 * 9/2018 ......... G01N 33/6896

OTHER PUBLICATIONS

Gordon et al., "Exposing and Modeling Underlying Mechanisms in ALS with Machine Learning," 2016 23rd International Conference on Pattern Recognition (ICPR), Cancun Center, Cancun, Mexico, Dec. 4-8, 2016. (Year: 2016).*

(Continued)

*Primary Examiner* — Jonathon A. Szumny
(74) *Attorney, Agent, or Firm* — Dorsey & Whitney LLP

(57) ABSTRACT

An integrated system and method for personalized stratification and prediction of neurodegenerative disease state and progression rate. Homogenous patient clusters are identified among heterogeneous patient data. Each patient cluster is characterized by specific disease factors that are used to predict disease progression state and rate for patients assigned to a particular patient cluster in accordance with his disease profile.

20 Claims, 31 Drawing Sheets

(56) References Cited

U.S. PATENT DOCUMENTS

2014/0236621 A1 8/2014 Six et al.
2018/0150609 A1 5/2018 Kim et al.

OTHER PUBLICATIONS

Drysdale et al., "Resting-state connectivity biomarkers define neurophysiological subtypes of depression," Nature Medicine vol. 23 | No. 1 | Jan. 2017; doi:10.1038/nm.4246 (Year: 2017).*

Kuffner et al., "Crowdsourced analysis of clinical trial data to predict amyotrophic lateral sclerosis progression," Nature Biotechnology vol. 33 No. Jan. 1, 2015; doi:10.1038/nbt.3051. (Year: 2015).*

Novakova et al., "Searching for neurodegeneration in multiple sclerosis at clinical onset: Diagnostic value of biomarkers," PLoS ONE 13(4): e0194828. https:// doi.org/10.1371/journal.pone. 0194828. (Year: 2018).*

Pfohl et al., "Unraveling the Complexity of Amyotrophic Lateral Sclerosis Survival Prediction," Front. Neuroinform. 12:36. doi: 10.3389/fninf.2018.00036. (Year: 2018).*

Ferro Pires, "A Supervised Learning Approach for Prognostic Prediction in ALS using Disease Progression Groups and Patient Profiles," Mestrado em Bioinformática e Biologia Computacional Especialização em Bioinformática Dissertação orientada por Profª. Doutora Sara Alexandra Cordeiro Madeira, 2018. (Year: 2018).*

Yang et al., "Identifying the Clusters within Nonmotor Manifestations in Early Parkinson's Disease by Using Unsupervised Cluster Analysis," PLoS ONE 9(3): e91906. doi:10.1371/journal.pone. 0091906. (Year: 2014).*

Szeto et al., "The relationships between mild cognitive impairment and phenotype in Parkinson's disease," npj Parkinson's Disease (2015) 1, 15015; doi:10.1038/npjparkd.2015.15. (Year: 2015).*

Sasaki et al., "Stratification of disease progression in a broad spectrum of degenerative cerebellar ataxias with a clustering method using MRI-based atrophy rates of brain structures," Cerebellum & Ataxias (2017) 4:9; DOI 10.1186/s40673-017-0068-4. (Year: 2017).*

Erro et al., "The Heterogeneity of Early Parkinson's Disease: A Cluster Analysis on Newly Diagnosed Untreated Patients," PLoS ONE 8(8): e70244. doi:10.1371/journal.pone.0070244. (Year: 2013).*

Bailly, et al., "Obstructive Sleep Apnea: A Cluster Analysis at Time of Diagnosis", PLOS One, Jun. 2016, pp. 1-12.

Gordon, et al., "Exposing and Modeling Underlying Mechanisms in ALS with Machine Learning", 2016 23rd International Conference on Pattern Recognition (ICPR) IEEE: 2168-2173. XP033085908, DOI: 10.1109/ICPR.2016.7899957, Dec. 2016, pp. 2169-2174.

Tang, et al., "Model-Based and Model-Free Techniques for Amyotrophic Lateral Sclerosis Diagnostic Prediction and Patient Clustering", Neuroinformatics, 17(3): 407-421. XP036820037. DOI: 10.1007/S12021-018-9406-9, Jul. 2019, pp. 1-29.

Xue, et al., "Incentivizing High Quality Crowdsourcing Clinical Data for Disease Prediction", 2017 IEEE/ACM International Conference on Connected Health: Applications, Systems and Engineering Technologies (Chase), 2017, pp. 185-194.

* cited by examiner

CLUSTER-BASED PREDICTION Classifier Training Ordinal

Speech

| Predicted | Actual | | | | |
|---|---|---|---|---|---|
| | 0 | 1 | 2 | 3 | 4 |
| 0 | 89 | 10 | 10 | 17 | 9 |
| 1 | 6 | 46 | 6 | 13 | 7 |
| 2 | 9 | 6 | 95 | 7 | 6 |
| 3 | 9 | 8 | 10 | 148 | 14 |
| 4 | 13 | 6 | 19 | 42 | 162 |

Respiratory

| Predicted | Actual | | | | |
|---|---|---|---|---|---|
| | 0 | 1 | 2 | 3 | 4 |
| 0 | 5 | 1 | 1 | 4 | 7 |
| 1 | 0 | 30 | 5 | 11 | 18 |
| 2 | 1 | 4 | 78 | 22 | 9 |
| 3 | 1 | 10 | 9 | 227 | 33 |
| 4 | 0 | 3 | 14 | 40 | 234 |

Salivation

| Predicted | Actual | | | | |
|---|---|---|---|---|---|
| | 0 | 1 | 2 | 3 | 4 |
| 0 | 32 | 2 | 5 | 4 | 29 |
| 1 | 4 | 30 | 3 | 10 | 22 |
| 2 | 5 | 5 | 65 | 15 | 33 |
| 3 | 6 | 5 | 10 | 116 | 44 |
| 4 | 3 | 3 | 11 | 41 | 264 |

Swallowing

| Predicted | Actual | | | | |
|---|---|---|---|---|---|
| | 0 | 1 | 2 | 3 | 4 |
| 0 | 47 | 2 | 4 | 17 | 11 |
| 1 | 4 | 35 | 4 | 14 | 9 |
| 2 | 3 | 6 | 66 | 19 | 15 |
| 3 | 8 | 3 | 10 | 149 | 20 |
| 4 | 3 | 2 | 23 | 45 | 227 |

Handwriting

| Predicted | Actual | | | | |
|---|---|---|---|---|---|
| | 0 | 1 | 2 | 3 | 4 |
| 0 | 162 | 8 | 16 | 19 | 3 |
| 1 | 10 | 65 | 4 | 4 | 1 |
| 2 | 9 | 9 | 97 | 14 | 3 |
| 3 | 5 | 22 | 12 | 202 | 4 |
| 4 | 3 | 11 | 6 | 25 | 40 |

Cutting Food

| Predicted | Actual | | | | |
|---|---|---|---|---|---|
| | 0 | 1 | 2 | 3 | 4 |
| 0 | 182 | 29 | 10 | 9 | 6 |
| 1 | 24 | 152 | 9 | 3 | 4 |
| 2 | 15 | 17 | 75 | 5 | 2 |
| 3 | 15 | 15 | 10 | 75 | 3 |
| 4 | 12 | 15 | 13 | 14 | 47 |

Dressing/Hygiene

| Predicted | Actual | | | | |
|---|---|---|---|---|---|
| | 0 | 1 | 2 | 3 | 4 |
| 0 | 169 | 37 | 17 | 8 | 2 |
| 1 | 13 | 157 | 18 | 2 | 1 |
| 2 | 14 | 18 | 126 | 7 | 2 |
| 3 | 15 | 15 | 18 | 74 | 2 |
| 4 | 14 | 12 | 4 | 9 | 13 |

Turning in Bed

| Predicted | Actual | | | | |
|---|---|---|---|---|---|
| | 0 | 1 | 2 | 3 | 4 |
| 0 | 95 | 22 | 16 | 14 | 1 |
| 1 | 10 | 134 | 18 | 17 | 1 |
| 2 | 7 | 14 | 112 | 11 | 4 |
| 3 | 10 | 17 | 13 | 106 | 4 |
| 4 | 7 | 12 | 24 | 23 | 49 |

Walking

| Predicted | Actual | | | | |
|---|---|---|---|---|---|
| | 0 | 1 | 2 | 3 | 4 |
| 0 | 73 | 7 | 29 | 1 | 2 |
| 1 | 6 | 115 | 18 | 4 | 1 |
| 2 | 5 | 11 | 290 | 8 | 2 |
| 3 | 7 | 12 | 42 | 55 | 3 |
| 4 | 7 | 8 | 23 | 8 | 30 |

Climbing Stairs

| Predicted | Actual | | | | |
|---|---|---|---|---|---|
| | 0 | 1 | 2 | 3 | 4 |
| 0 | 333 | 23 | 3 | 1 | 4 |
| 1 | 74 | 152 | 1 | 4 | 2 |
| 2 | 23 | 3 | 13 | 0 | 2 |
| 3 | 30 | 11 | 2 | 25 | 1 |
| 4 | 23 | 7 | 0 | 3 | 27 |

FIG. 14

TEMPORAL PREDICTION OF DISEASE STATE AND PROGRESSION RATE Data Enrichment

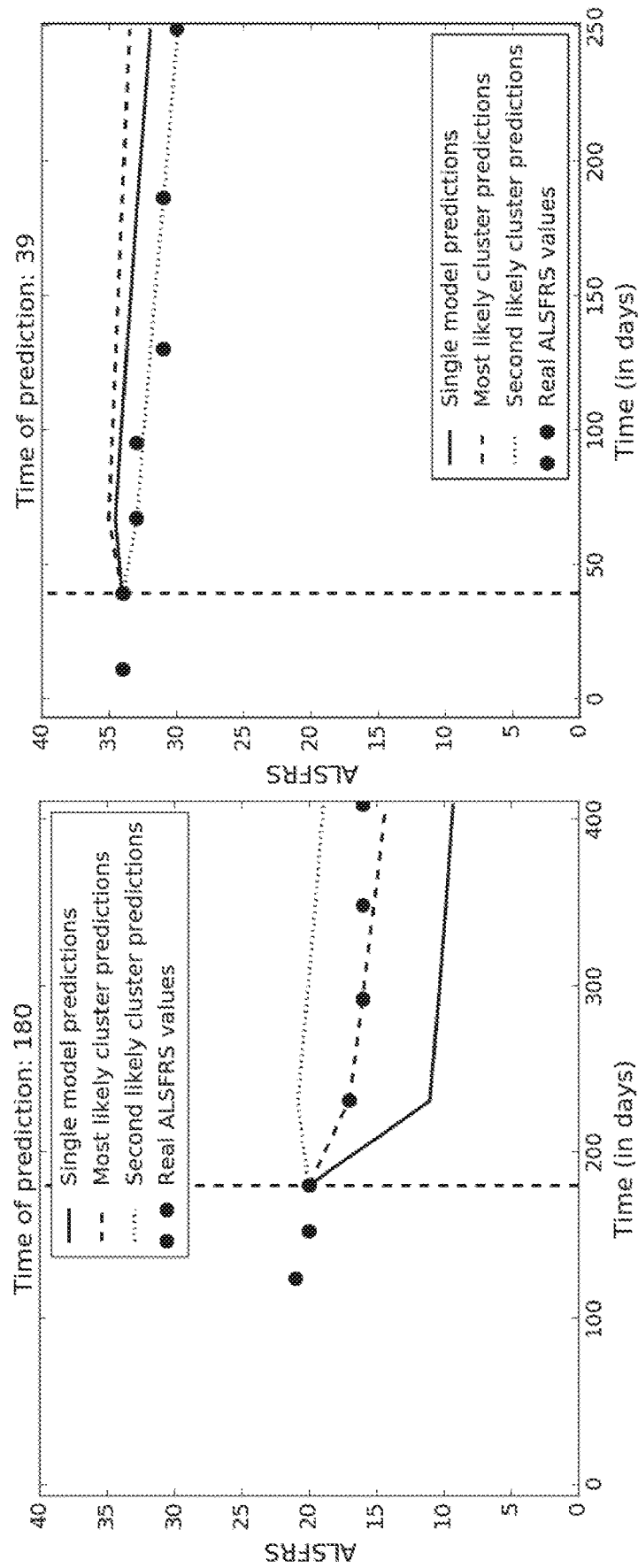

INTEGRATED SYSTEM AND METHOD FOR PERSONALIZED STRATIFICATION AND PREDICTION OF NEURODEGENERATIVE DISEASE

CROSS-REFERENCE TO RELATED APPLICATIONS

This application is a National Phase Application of PCT International Application No. PCT/IL2018/051340, International Filing Date Dec. 6, 2018, which is hereby incorporated by reference.

BACKGROUND OF THE INVENTION

Neurodegenerative Diseases (NDs) are devastating illnesses lacking significant effective therapies. The diseases are heterogeneous; their onset site and progression pattern can differ significantly among patients. There are no well-known methods of tracking disease progression because of the lack of known specific biomarkers that are good predictors of future disease state or deteriorative progression rate. Consequently, physicians cannot effectively assess disease state at a future point in time. In addition, when running clinical trials for developing therapies, there is a lack of effective tools for selecting patients with similar deterioration profiles; thus, a large sample of patients is required which significantly increases trial duration and cost.

Therefore, there is a need to identify effective methods of characterizing heterogeneous NDs thereby facilitating treatment by medical practitioners and development of therapeutic drugs by drug developers.

SUMMARY OF THE INVENTION

According to the teachings of the present invention there is provided a method for predicting Neurodegenerative Disease (ND) progression rate performed on a computing device having a processor, memory, and one or more code sets stored in the memory and executed in the processor, the method including receiving feature-based representation of ND patients; hierarchically clustering individual Functionality Measure (FM) items into group FM items, the clustering implemented on a basis of most closely correlating individual FM item values; grouping individual FM items into body function groups in accordance with group FM items; calculating group FM item progression rates for each of the body function groups; establishing a multi-dimensional patient representation based on the group FM item progression rates; clustering the multi-dimensional patient representation into distinct patient clusters; identifying an optimal number of patient clusters from among patient data in accordance with data driven optimization scheme; and predicting a progression rate for a new patient in accordance with a patient cluster of the distinct patient clusters to which the new patient is assigned.

According to a further feature of the present invention, the progression rate is characterized by an individual progression rate, a group progression rate, or a total progression rate.

According to a further feature of the present invention, there is also provided identifying at least one factor associated with each of the plurality of patient clusters.

According to a further feature of the present invention, the identifying at least one factor is implemented through statistic-based factor identification.

According to a further feature of the present invention, the identifying at least one factor is implemented through classifier-based factor identification.

According to a further feature of the present invention, the identifying at least one factor is further implemented through classifier-based factor identification.

According to a further feature of the present invention, the identifying at least one factor is implemented through causal-based factor identification.

According to a further feature of the present invention, the identifying at least one factor is further implemented through causal-based factor identification.

According to a further feature of the present invention, the identifying the at least one factor is further implemented through causal-based factor identification.

According to a further feature of the present invention, there is also provided training a plurality of cluster-specific classifiers, each of the classifiers operative in accordance with the at least one factor associated with its respective patient cluster of the plurality of patient clusters.

According to a further feature of the present invention, the plurality of cluster-specific classifiers are implemented as ordinal classifiers.

According to a further feature of the present invention, the plurality of cluster-specific classifiers are implemented as Bayesian network classifiers.

According to a further feature of the present invention, there is also provided assigning a new patient to one of the patient clusters in accordance with a best match between a progression rate of the new patient and a progression rate of any of the patient clusters.

There is also provided according to the teachings of the present invention, an integrated system for predicting Neurodegenerative Disease (ND) progression rate, the system including an input device operative to receive feature-based patient representations; a computing device configured to: identify an optimal number of patient clusters from among patient data in accordance with a data driven optimization scheme; assign a new patient to one of the patient clusters in accordance with a best match between a progression rate of the new patient and a progression rate of any of the patient clusters; predict a progression rate for the new patient in accordance with the one patient cluster to which the new patient is assigned, the progression rate comprising individual progression rate, group progression rate, or total progression rate; and an output device operative to output the progression rate.

According to a further feature of the present invention, configured to calculate a predicted disease state in accordance with the predicted progression rate, the predicted disease state comprising an individual Functionality Measure (FM) item value, a group FM item value, or a total FM item value.

According to a further feature of the present invention, there is also provided the computing device is further configured to train a plurality of cluster-specific classifiers, each of the classifiers operative in accordance with the at least one factor associated with its respective patient cluster of the plurality of patient clusters.

There is also provided according to the teachings of the present invention, a method for predicting Neurodegenerative Disease (ND) state performed on a computing device having a processor, memory, and one or more code sets stored in the memory and executed in the processor, the method including: receiving feature-based representation of ND patients, the feature-based representation including static and dynamic features; randomly assigning a plurality of patients among a plurality of patient clusters, each patient represented with static and dynamic features; training a long short-term memory (LSTM)-based classifier for each patient cluster, each respective classifier operative to predict a disease state for a plurality of patients of an associated patient cluster; and iteratively running a training cycle until a performance measure is achieved, the training cycle including: testing a disease state of a plurality of patients with each of the respective classifiers, reassigning at least one patient to a patient cluster best matching his disease state, and retraining each of the respective classifiers using a plurality of patients now associated with each of the patient clusters; and predicting disease state of the new patient in accordance with the cluster to which the new patient is assigned, the disease state characterized by FM value of the cluster.

According to a further feature of the present invention, the feature-based patient representation is based on an FM value and feature representations of a combinatorial combination of previously observed data points.

According to a further feature of the present invention, there is also provided assigning a new patient to a patient cluster in accordance with a cluster-specific prediction most closely matching a general non-cluster prediction model based on all patients.

There is also provided according to the teachings of the present invention, a system for predicting Neurodegenerative Disease (ND) state and progression rate, the system including an input device operative to receive feature-based representation of ND patients, the feature-based representation including static and dynamic features; a computing device configured to: randomly assign a plurality of patients among a plurality of patient clusters, each patient represented with static and dynamic features, train a long short-term memory (LSTM)-based classifier for each patient cluster, each respective classifier operative to predict a disease state for a plurality of patients of an associated patient cluster, and iteratively run a training cycle until a performance measure is achieved, the training cycle including testing a disease state of a plurality of patients with each of the respective classifiers, reassigning at least one patient to a patient cluster best matching his disease state, and retraining each of the respective classifiers using a plurality of patients now associated with each of the patient clusters; predict disease state of the new patient in accordance with the cluster to which the new patient is assigned, the disease state characterized by Functionality Measure (FM) value of the cluster; and an output device operative to output the disease state.

According to a further feature of the present invention, the feature-based patient representation is based on an FM value and feature representations of a combinatorial combination of previously observed data features.

According to a further feature of the present invention, the computing device is further configured to assign a new patient to a patient cluster in accordance with a cluster-specific prediction most closely matching a general non-cluster prediction model based on all patients.

According to a further feature of the present invention, the computing device is further configured to predict disease state of the new patient in accordance with the cluster to which the the new patient is assigned, the disease state characterized by FM value of the cluster.

BRIEF DESCRIPTION OF THE DRAWINGS

The subject matter regarded as the invention is particularly pointed out and distinctly claimed in the concluding portion of the specification. The features, method of operation, and advantages are set forth in the following description and accompanying drawings in which:

FIG. 14 depicts confusion matrices for each of the ALSFRS items when predicting disease state using only information from the first clinic visit, in accordance with an embodiment;

FIGS. 21A-21B are predictions of the disease trajectory of a single model, most likely cluster, and second most likely cluster for two arbitrary patients from the test set in comparison to the real ALSFRS values, in accordance with an embodiment.

Figure 1:
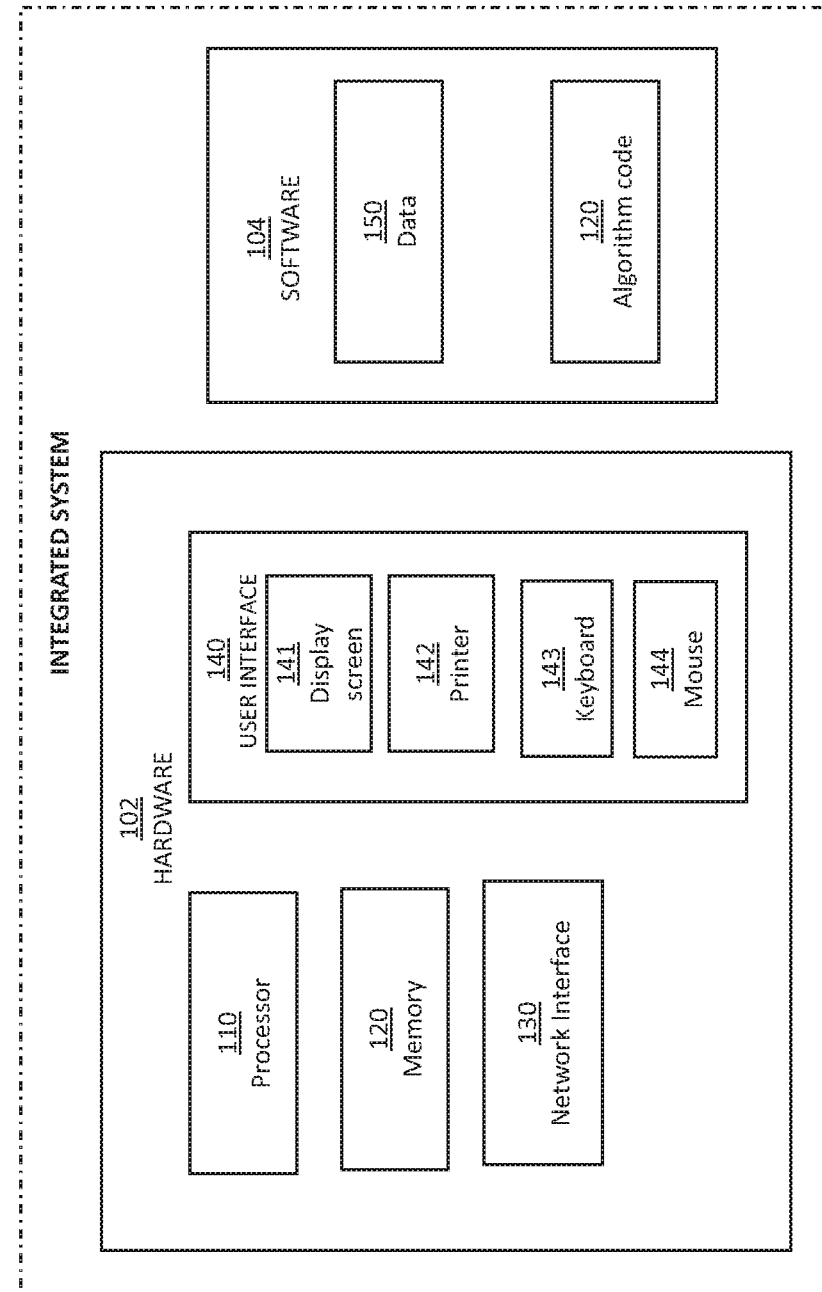
FIG. 1 is a block diagram of the integrated system for personalized stratification and prediction of ND, in accordance with a first embodiment.

It will be appreciated that for simplicity and clarity of illustration, figure elements are not necessarily drawn to scale. Furthermore, where appropriate, reference numerals are repeated among the figures to indicate corresponding or analogous elements.

DETAILED DESCRIPTION

In the following description, numerous details are set forth to provide a thorough understanding of the invention. However, it will be understood by those skilled in the art that the present invention may be practiced without these specific details. Furthermore, well-known methods, procedures, and components have not been described in detail to highlight the present invention.

The present invention is an integrated system and method for personalized stratification and prediction of neurodegenerative disease. The integrated system has application in various neurologically degenerative diseases like Alzheimer, Parkinson's disease, Amyotrophic Lateral Sclerosis (ALS). It should be appreciated that each neurodegenerative disease has its unique set of functionality measure (FM) items used to characterize disease state as set forth in the listing below.

| ND | Functionality measures (FM) |
| --- | --- |
| Alzheimer's Disease | 1) Clinical status with values: cognitively normal (CN), mild cognitive impairment (MCI), probable Alzheimer's Disease (AD) 2) ADAS-Cog score, which are cognitive scores of AD, composed of 13 questionnaires 3) Ventricles volume |
| Parkinson' Disease | No specific test exists. Diagnosis based on medical history, signs/symptoms review, and physical examination |
| ALS | ALS functional rating scale (ALSFRS) for 10-12 functions with values for each between 4 (normal functionality) and 0 (no functionality), where the total ALSFRS(-R) is in 0-40(48) |

Without diminishing in scope, the system will be discussed in the context of ALS.

The ten ALSFRS items, or in the case of the ALSFRS-R twelve items, describe physical functionalities of the patient, e.g., breathing, speaking, and walking, as noted above and listed later in Table 1. Each ALSFRS item is assigned a value between 0 for no functionality and 4 for full functionality. Grouping combinations of individual ALSFRS items together into a particular body function group is characterized by a group ALSFRS value. Accordingly, ALSFRS item values can be implemented as either individual, group, or total values in accordance with the configuration of integrated system 100. As noted above, the heterogeneity of disease progression with relation to both rate and pattern significantly complicates in amyotrophic lateral sclerosis. Issues such as disease onset site, progression rate, and pattern of progression vary greatly among patients so that it is often extremely difficult to reach statistically sound conclusions in clinical trials, and large numbers of participants are required for these.

In the past, conventional prediction systems have attempted to find meaningful sub-groups among patient population by concentrating on specific features such as family history, onset site, or disease progression rate.

Furthermore, conventional prediction systems assume linear disease progression and therefore employ a linear statistical model for regression, evaluated by its accuracy/error in predicting a future progression rate of the patient (total) ALSFRS value. Recently, machine-learning (ML) classifiers, such as the random forest, were used to predict progression rate, dispensing with the linearity assumption. The integrated system also dispenses with the linearity assumption, and together with predicting progression rate, it also predicts patient disease state. Both system predictions are of individual, group, and total ALSFRS item values, as noted above. Group and individual ALSFRS item prediction advantageously provides greater prediction resolution than prediction of the (total) ALSFRS employed in conventional systems.

Conventional systems concentrate on progression rate prediction for the heterogeneous patient population using statistical or ML methods such as regression. One way the integrated system predicts progression rate is for each of homogenous subpopulation clusters stratified by the system from the population, as will be further discussed. The integrated system also predicts disease state (ALSFRS value) either by a classifier or by temporal modeling. Based on disease state prediction, a second way the system predicts progression rate is by considering the difference between predicted disease states in specified time points divided by their time duration.

For the sake of this document, data obtained from the Pooled Resource Open-Access Clinical Trial (PRO-ACT) database of ALS patient data is employed to test the integrated system. It should be appreciated that the integrated system can process analogous patient data bases representing various types of ND. Furthermore, it should be appreciated that the term "best match" is a context specific term and is therefore implemented in accordance with context.

Turning now to the figures, FIG. 1 is schematic, block diagram of an embodiment of an integrated system 100 for personalized stratification and prediction of ND recognition. Integrated system 100 includes at least one processor 110 operative to execute one or more code sets, memory 120 operative to store the code sets and various data types, a network interface 130 enabling network functionality, user interface devices 140 like display screen 141, printers 142, keyboard 143, mouse 144, plus other user interface accessories.

As shown, system 100 includes a software module 104 including a database 105 of various types of patient data and a module of algorithm code 120 operative to process patient data. Code 120 must be executed by processor 110.

Figure 2A:
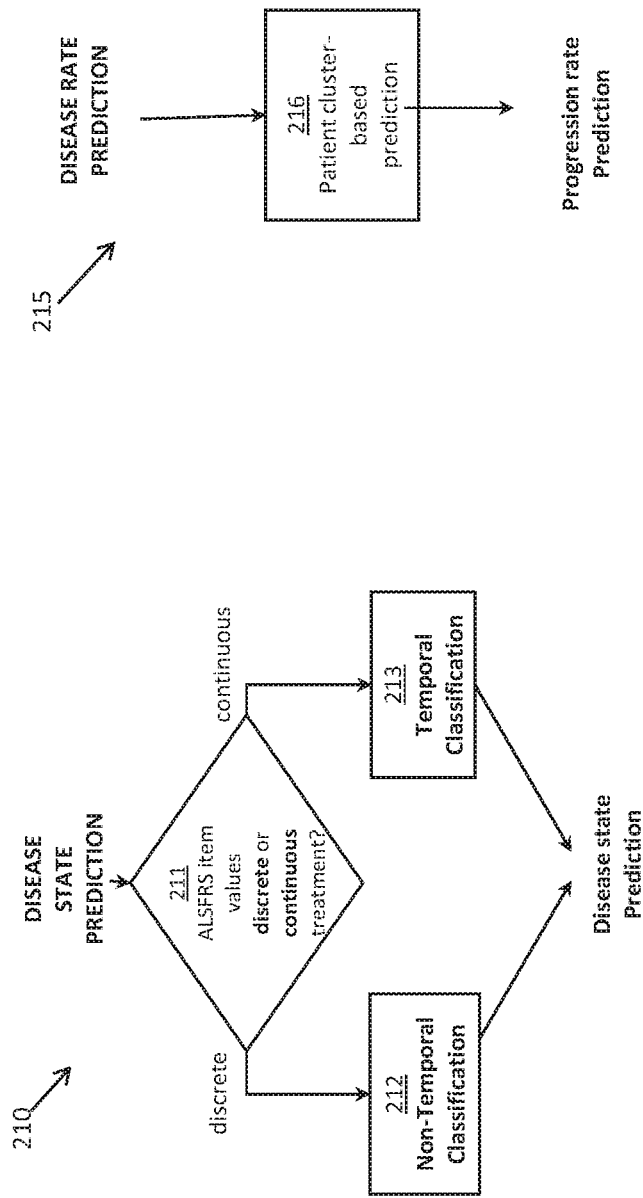
FIG. 2A depicts a general flow chart of two processing goals, (embodiments) of the integrated system.

FIG. 2A is a comparison of two processing goals for which integrated system 100 is operative to achieve in accordance with configuration settings. As shown, process 210 is directed to disease state prediction and process 215 is directed to prediction of progression rate.

Specifically, disease state prediction 210 includes a decision step 211 in which user supplied configuration directs processing to either treat patient data discreetly or as a continuous data unit in which all patient data spanning the duration of clinic visits is processed as a unit. If patient data is treated discreetly, processing continues to step 212 where various forms of non-temporal classification is implemented to provide the disease state prediction. Non-temporal classifiers are simple and easy and fast to train and test new patients but do not use all available longitudinal data. Predicted disease states can readily be converted into prediction rates by dividing the difference in predicted state scores by the time span between them.

Alternatively, when patient data is treated through temporal classification, processing proceeds to step 213 to also provide disease state prediction. Temporal classification uses all available longitudinal data, but it is complex and slow for training and testing new patients.

Processing directed to prediction of disease progression rate in step 215 relies on the integrated system on patient cluster-based prediction 216 as will be further discussed.

Figure 2B:
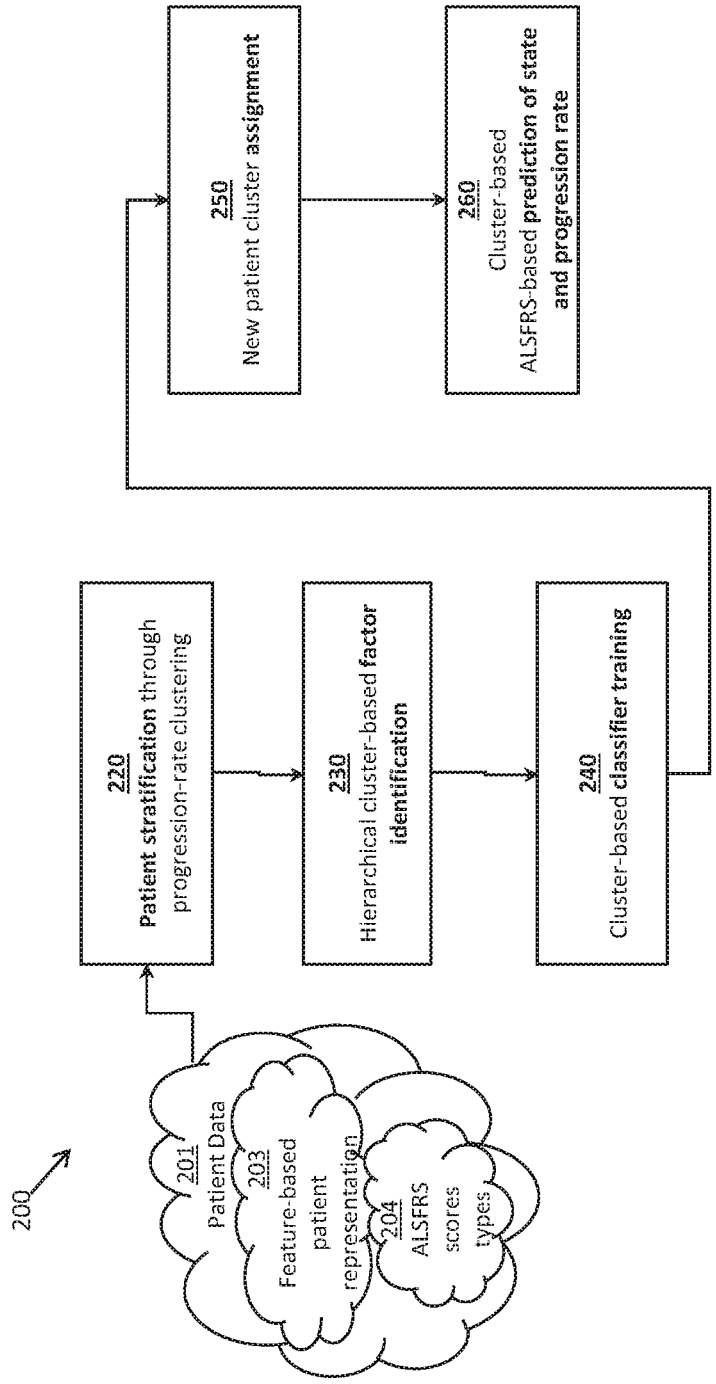
FIG. 2B depicts a general flow chart of primary steps employed predicting disease progression and state, in accordance with a first embodiment.

FIG. 2B depicts a general flow chart of primary steps employed by integrated system 100 to predict disease state and progression, in accordance with a first embodiment based on first identifying patient clusters and then implementing cluster-specific prediction.

Specifically, clinical patient data 201 is provided and includes feature-based representation 203, generated in preliminary a data processing step to remove outliers and handle missing data from a portion of the usable patient data, and individual ALFSFRS values 204. In step 220 patient data 201 is stratified into characteristic clusters. In step 230, factors for each of the identified clusters are identified. In step 240, a classifier is trained in accordance with characterizing features of each respective patient cluster. In step 250, a new patient is assigned to the patient cluster best matching his progression rate. In step 260, integrated system generates cluster-based ALSFRS item prediction values characterizing expected disease state and progression rate, for either individual, group, or total ALSFRS values.

Patient Stratification

Figure 3:
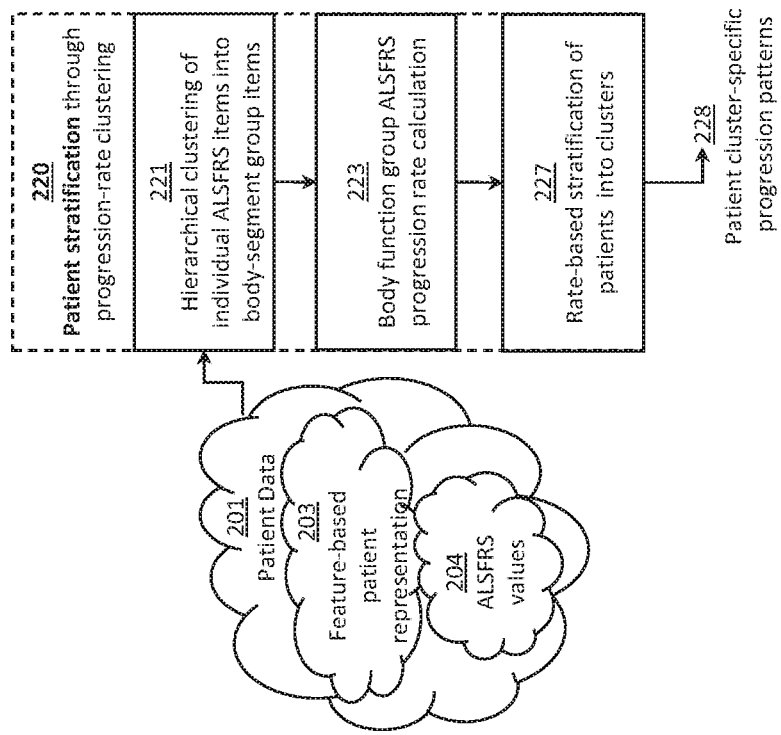
FIG. 3 depicts the processing steps implementing the patient stratification step 220 of FIG. 2, in accordance with an embodiment.

FIG. 3 depicts the processing steps implementing progression rate-based stratification step 220 of FIG. 2, in accordance with an embodiment. Specifically, in step 221 a hierarchical clustering is employed to identify group ALSFRS items from correlation values between pairs of individual ALSFRS items values from ALSFRS item values data 204.

Figure 4A:
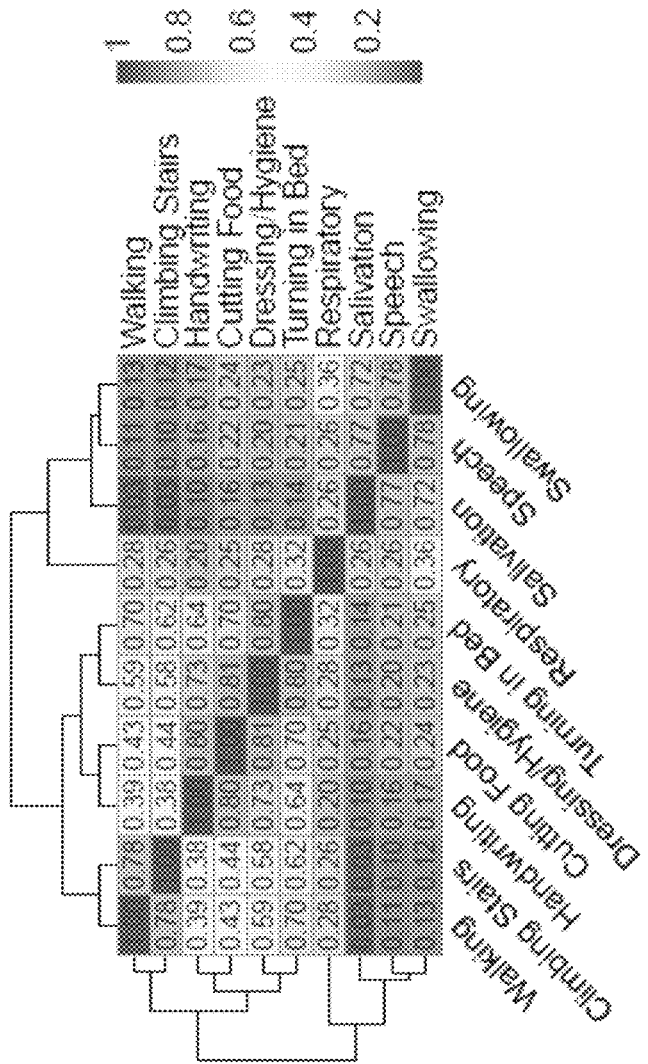
FIG. 4A is a hierarchical clustering to identify group ALSFRS items from correlation values between pairs of individual ALSFRS, according to an embodiment.

By way of example, FIG. 4A depicts a correlation matrix of the (Pearson product-moment) correlation coefficient values between pairs of the individual ALSFRS items for all patients in the PRO-ACT database during their last documented clinic visit. For ten ALSFRS items, the correlation matrix provides correlation values for 45 pairs of items. Note that other measures of correlations (e.g., rank, distance) are appropriate too. Also, FIG. 4A shows a dendrogram which is the result of hierarchical clustering of these items. Grouping by hierarchical clustering is implemented by the degree of similarity between correlation values, which decreases as clustering progresses hierarchically from leaves to root.

Such clustering facilitates grouping the ten individual ALSFRS items into five body function groups associated with five body parts. In the first instance, Walking is grouped with Climbing Stairs (because they are similar to each other more than to any third item), Handwriting with Cutting Food (ditto), Dressing with Turning in Bed, and Speech with Swallowing, and immediately after that the two are combined with Salivation. Respiratory has, in the beginning, no similarity to any of the items and thus remains a group of itself. This leads to five groups: Lower limbs, Upper limbs, Full body, Bulbar, and Respiratory, respectively, as set forth in Table 1 below:

TABLE 1

A higher level grouping of ALSFRS items based on the PROACT data.

| ALSFRS functions | Semantic interpretation |
| --- | --- |
| Salivation, Speech, Swallowing | Bulbar |
| Handwriting, Cutting Food and Eating | Upper limbs |
| Walking, Climbing Stairs | Lower limbs |
| Turning in Bed, Dressing and Hygiene | Full body |
| Respiratory | Respiratory |

This grouping reduces the dimension of disease state representation and facilitates stratification of patients into sub-groups, or clusters, thereby enabling characterization through a lower-dimensional feature vector derived from the sum of ALSFRS items for each of the five groups instead of viewing disease progression deterioration in a scalar entity represented by the linear slope (rate) of the sum of ALSFRS values as done in conventional disease predictors. Patient representation has not necessarily be five-dimensional for five body function groups, but it can be multidimensional between 2 and 9 groups (because 1 group is identical to the total ALSFRS, and 10 groups is identical to the individual ALSFRS items).

In step 223, ALSFRS progression rates are calculated for each of the five body function groups in accordance with formula (1) below:

$$\Delta Group_{j,T_{k,l}} = \frac{Group_{j,T_k} - Group_{j,T_l}}{T_k - T_l}; T_k > T_l, j \in \{1, 5\} \quad (1)$$

where $Group_{j,T_i}$ corresponds to the sum of ALSFRS values belonging to $Group_j$ at time $T_i$. For example, this rate is computed with k corresponding to the end of the first year documented for the patient and l to the beginning of the year for patients and constructed a feature representation for each patient of a patient population of 2,475 of the PRO-ACT database for which it was possible to calculate the rates for the five groups during the first year. Group progression rates are then combined to form a patient multi-dimensional (five-dimensional in the case of formula 1) vector representation. In step 227, clustering the multi-dimensional patient representation into distinct patient clusters using the k-means algorithm and the Euclidean distance metric allows progression-rate-based stratification of the patients into clusters.

Figure 4B:
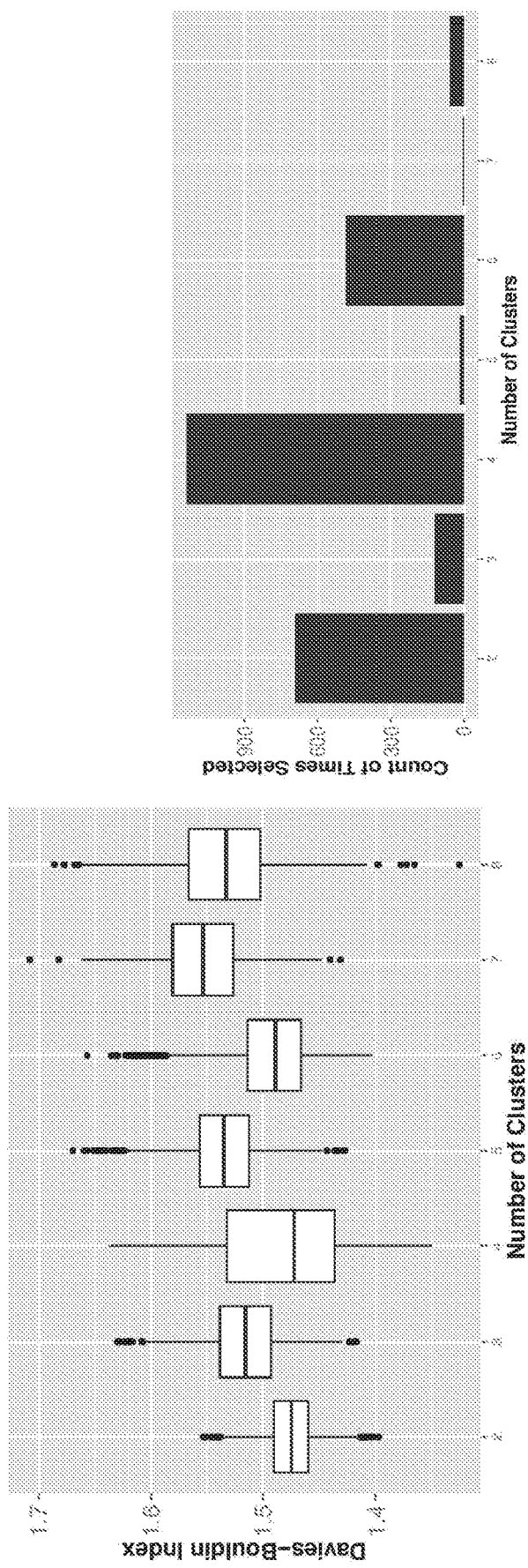
FIG. 4B is a boxplot for Davies-Bouldin index (DBI) and histogram, left and right respectively, of the value selected by DBI as a function of the number of clusters (k), recommending the selection of four patient clusters based on the data, in accordance with an embodiment.

FIG. 4B depicts that optimization to get the best clustering scheme using 2,500 bootstrapped patient populations (with 60% of the patients in each sample) identified that four clusters were the most appropriate number of clusters. This four-cluster clustering scheme optimized (minimized) the average Davies-Bouldin index (DBI) (left) and was selected the best scheme (with respect to DBI minimization) in most times (right). Note that the DBI evaluates clustering schemes based on internal measures of cluster compactness and between cluster distances, recommending a scheme having clusters that are most highly compact and distanced from each other. Other data-driven optimized measures than the DBI can be applied too, e.g., the Dunn index or Silhouette index, which similarly to the DBI, measure how well clusters in each clustering scheme are simultaneously compact and well separated. Applying this generic optimization approach to another ALS database or a database representing another ND would yield the optimal number of clusters for that database.

Each cluster centroid, representing all cluster patterns, is easily interpretable as a distinct disease progression pattern as set forth in Table 2 below.
As shown, the total progression rates calculated for the four patient clusters, or sub-groups, have different values:

TABLE 2

Cluster centroids represented as vectors of progression rates for five body function groups for four selected patient clusters

| Cluster ID | Bulbar | Upper limbs | Lower limbs | Full body | Respiratory | Total |
|---|---|---|---|---|---|---|
| 1 | −0.024 | −0.048 | −0.050 | −0.058 | −0.013 | −0.192 |
| 2 | −0.061 | −0.271 | −0.199 | −0.263 | −0.049 | −0.843 |
| 3 | −0.423 | −0.454 | −0.340 | −0.437 | −0.099 | −1.753 |
| 4 | −0.428 | −0.117 | −0.139 | −0.137 | −0.075 | −0.896 |

Cluster 1 represents slow disease progressors, with a total progression rate of ≈ −0.2 points per month,
Cluster 3 represents fast progressors, with a total progression rate of ≈ −1.75 points per month.
Clusters 2 and 4 represent moderate progressors ≈ −0.85 points per month.

However, cluster 2 is characterized by a rapid deteriorative progression rate in limb and body related functions but slow progression in bulbar related functions, in contrast to cluster 4 that is characterized by a rapid deterioration in bulbar functions and slow deteriorative progression rate in limb and body related functions. As shown, this disease characterization advantageously provides resolution of the responsible bodily and limb progression for the disease progression unavailable in conventional disease predictors based on a sum of all ALSFRS item values. This added resolution facilitates improved medical treatment and drug development for patients associated with each patient cluster. It should be appreciated that cluster progression rate is characterized by either a progression rate of the cluster centroid, as noted in Table 2, or as an average progression rate of the patients associated with the cluster, in accordance with the embodiment.

Figure 5:
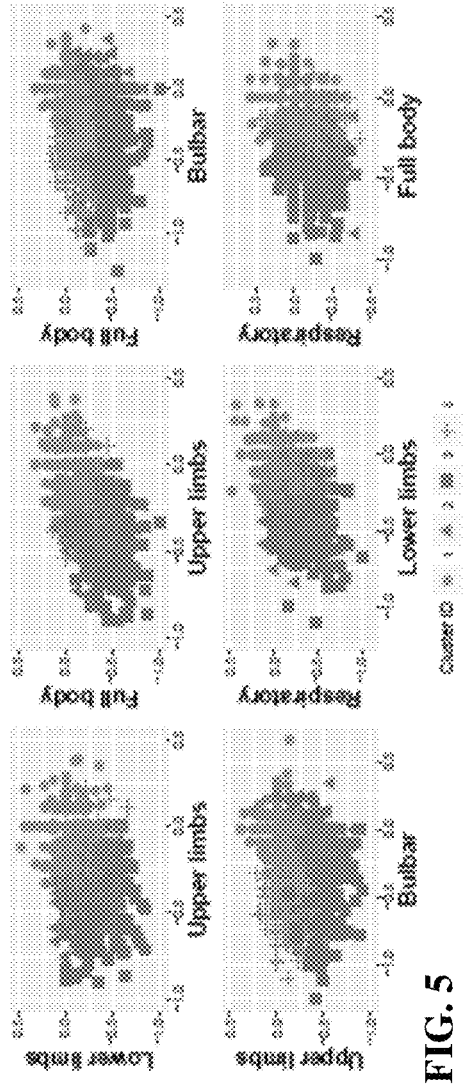
FIG. 5 depicts projections of the clustering schema onto six of the ten (for five body function group ALSFRS items) possible group two-dimensional scatter plots, according to an embodiment.

By way of example, FIG. 5 shows six of the ten possible two-dimensional spaces defined by the five ALSFRS body function groups. As shown, in some spaces, like these of Upper limb vs Bulbar, patients are more clearly separated, whereas other spaces are less informative like the spaces associated with Respiratory functionality. However, in all projections, a clear and similar partition emerges between different body function clusters occupying different regions of the space that characterizes different values of the group ALSFRS item values.

Figure 6:
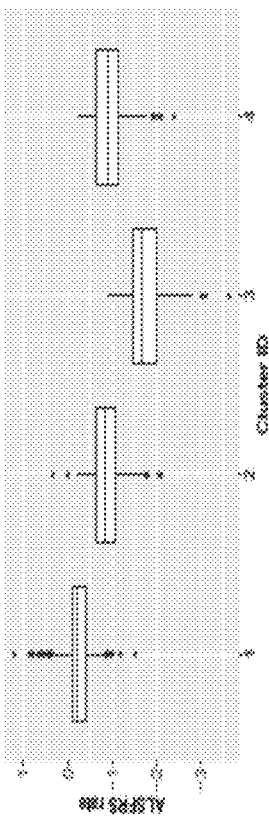
FIG. 6 is a boxplot for the sum of progression rates over a five body function group ALSFRS items for four identified patient clusters, according to an embodiment.

FIG. 6 shows the distribution of the sum of group rates over the clusters. Statistical testing shows that the pairwise differences between the sums of group rates of the clusters are significant (p-value<<0.01), with the exception of between clusters 2 and 4. As patients from these two clusters have similar total rates, the differences between them can only be exposed by examining their rates of the ALSFRS groups (i.e., progression patterns) rather than their ALSFRS summation as set forth in see Table 2 above for each cluster (i.e., Total in Table 2) and the cluster average and standard deviation of the total rate as computed over the patient rates for each cluster (when the total rate for a patient is summed over those of the five groups). As shown, the two values are very similar for each cluster, further implying that the cluster centroid aptly represents the patients assigned to the cluster. Also, the similar standard deviation values among the clusters imply similar statistical properties of the clusters.

Factor Identification

Figure 7:
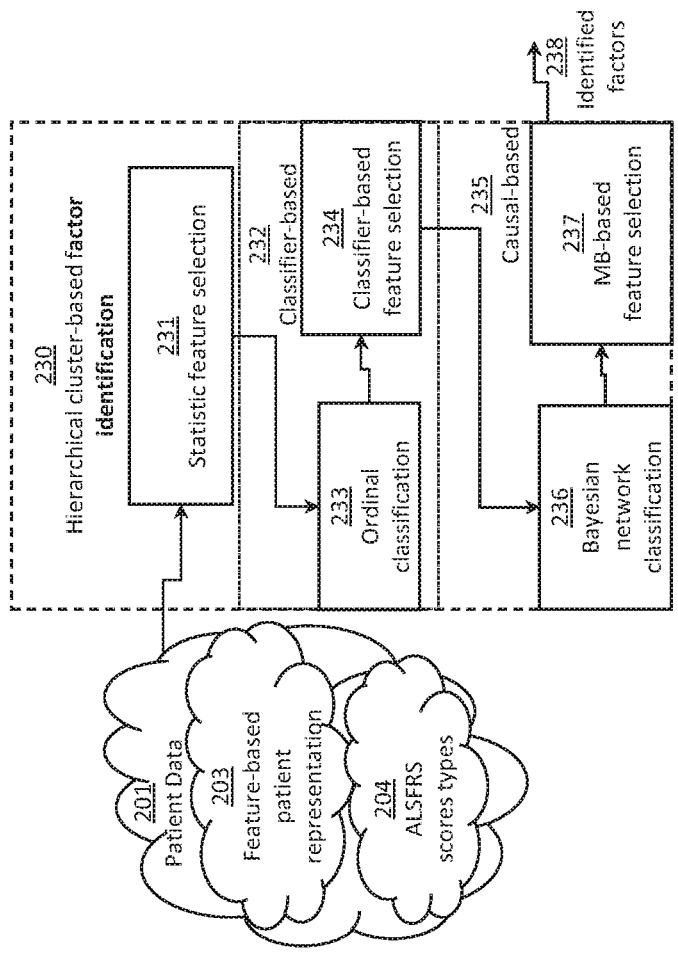
FIG. 7 depicts the processing steps implementing the hierarchical cluster-based factor identification step 230 of FIG. 2C, in accordance with an embodiment.

FIG. 7 depicts the processing steps implementing identification step 230 of FIG. 2, in accordance with an embodiment.

Statistic-Based Factor Identification

Specifically, in step 231, statistic factor identification is implemented (Algorithm 1) by utilizing the $J_3$ scatter criterion for feature selection, according to an embodiment. The $J_3$ scatter criterion is a measure to compare feature sub-sets of a given size, $k \in [1:K]$, K is the maximal feature sub set desired, and the accuracy of a classifier selects among the feature sub-sets of all sizes (each is $J_3$-optimized for a specific k) the one with the best feature sub set (as sub sets of different sizes are not $J_3$-comparable) Step 231 is repeated for each of the ten ALSFRS values.

Algorithm 1 is employed to determine the feature sub-set to be used when modeling the ALSFRS values of each item:

---
Algorithm 1: Feature selection by the $J_3$ criterion and classification
---
Input: Potential features, K the maximal feature sub-set size desired, and ALSFRS target value
Output: Selected feature sub-set for the ALSFRS target value
for k = 1:K do
    for Every possible feature sub-set of size k do
        Calculate $J_3$ scatter criterion with target variable;
        Let bestFeat(k) be feature sub-set of size k with the highest $J_3$;
    end
    Train a classifier with bestFeat(k) $\forall = 1 : K$ and calculate its accuracy on the test set;
end
Return: bestFeat(k) with the highest accuracy on the test set

---

Based on Algorithm 1, Table 3 below summarizes the participation of lab test variables in the selected lab test feature sub-sets for the ten ALSFRS items when the classifier was a two-layer perceptron neural network (with k/2 hidden units when k<10 for k features, and 10 hidden units otherwise) trained using the conjugate gradient and back-propagation algorithms. All lab test results that were not discarded due to missing data were included in the initial feature set, with K=25.

TABLE 3

Summary of lab test feature selection for each ALSFRS item

| | | Speech | Salivation | Swallowing | Handwriting | Cutting Food & Eating | Dressing/ Hygiene | Turning in Bed | Walking | Climbing Stairs | Respiratory |
|---|---|---|---|---|---|---|---|---|---|---|---|
| Laboratory Variable | Basophil | ✓ | ✓ | ✓ | | ✓ | ✓ | ✓ | ✓ | ✓ | ✓ |
| | Eosinophil | ✓ | ✓ | ✓ | ✓ | ✓ | ✓ | ✓ | ✓ | ✓ | ✓ |
| | Lymphocyte | ✓ | ✓ | ✓ | | ✓ | | | ✓ | ✓ | ✓ |
| | Monocyte | ✓ | ✓ | ✓ | | | ✓ | ✓ | | ✓ | ✓ |
| | Albumin | ✓ | ✓ | ✓ | | ✓ | ✓ | ✓ | | ✓ | ✓ |
| | Alkaline Phosphatase | ✓ | ✓ | ✓ | | ✓ | ✓ | ✓ | ✓ | ✓ | ✓ |
| | ALT | ✓ | ✓ | ✓ | | ✓ | ✓ | ✓ | ✓ | ✓ | ✓ |
| | AST | ✓ | ✓ | ✓ | | ✓ | ✓ | ✓ | ✓ | ✓ | ✓ |
| | Bicarbonate | | | | | | | | | | |
| | Bilrubin | ✓ | ✓ | ✓ | | ✓ | ✓ | | ✓ | ✓ | ✓ |
| | BUN | ✓ | ✓ | ✓ | | ✓ | ✓ | ✓ | ✓ | ✓ | ✓ |
| | Calcium | ✓ | ✓ | ✓ | | ✓ | ✓ | ✓ | | ✓ | ✓ |
| | Chloride | ✓ | ✓ | ✓ | | ✓ | ✓ | ✓ | ✓ | ✓ | ✓ |
| | CK | ✓ | ✓ | ✓ | ✓ | ✓ | ✓ | ✓ | ✓ | ✓ | ✓ |
| | Creatinine | ✓ | ✓ | ✓ | ✓ | ✓ | ✓ | ✓ | ✓ | ✓ | ✓ |
| | Glucose | ✓ | | | | ✓ | ✓ | | | ✓ | ✓ |
| | Hematocrit | | ✓ | ✓ | | ✓ | ✓ | ✓ | ✓ | ✓ | ✓ |
| | Hemoglobin | ✓ | ✓ | ✓ | | ✓ | ✓ | | ✓ | ✓ | ✓ |
| | Phosphorus | ✓ | ✓ | ✓ | ✓ | ✓ | ✓ | ✓ | ✓ | ✓ | ✓ |
| | Platelets | | | | | ✓ | ✓ | | | | |
| | Potassium | | ✓ | ✓ | | ✓ | ✓ | | ✓ | ✓ | ✓ |
| | Protein | ✓ | ✓ | ✓ | | ✓ | ✓ | ✓ | | ✓ | ✓ |
| | Red Blood Cells | | | | | | | | | | |
| | Sodium | ✓ | ✓ | ✓ | | ✓ | ✓ | ✓ | | | ✓ |
| | White Blood Cells | | | | | | | | | | |

Table 3 shows that the algorithm for feature selection favors feature sub-sets that include most of the lab test variables. "Handwriting" is the exception to this, where the feature selection algorithm chose a feature set with only four of the laboratory variables. Furthermore, three of the variables (bicarbonate, red blood cells, and white blood cells) were not selected in any of the feature sub-sets.

Figure 8:
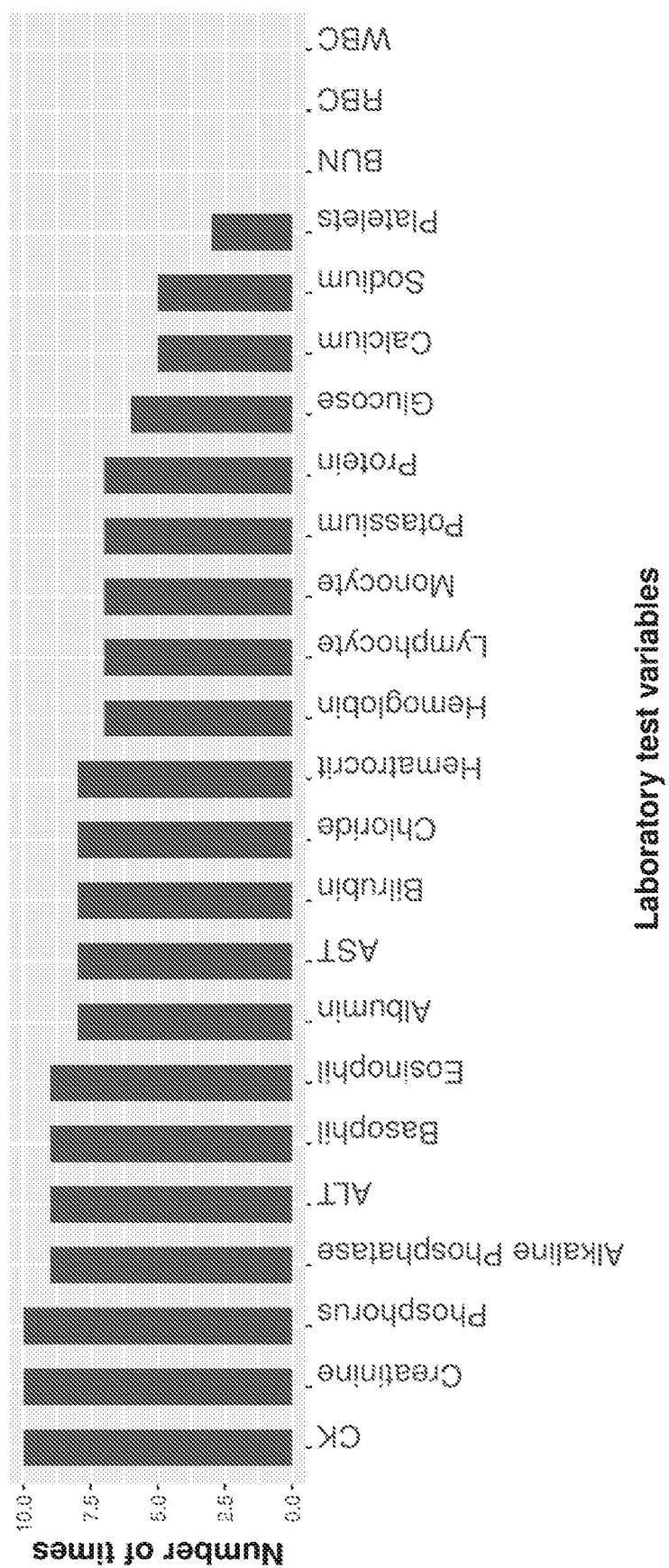
FIG. 8 depicts the number of times each lab test variable was selected by the statistic feature-selection algorithm as being a significant variable among the ten ALSFRS items, in accordance with an embodiment.

FIG. 8 depicts the number of times each lab variable was selected by the feature-selection algorithm as being a significant factor among each of the ten ALSFRS items.

Classifier-Based Factor Identification

Classifier-based factor selection 232 is implemented through training a classifier in step 233 to accomplish feature selection in step 234.

Specifically, in step 233, decision trees (DTs) are trained using the C5.0 algorithm, a tree for each of the ALSFRS items. The task is a five-class classification since ALSFRS is a target variable having values 0-4. The trees are trained, where the degree of pruning is determined empirically for each of the ALSFRS items using a validation set.

In step 234, for each ALSFRS item, variable importance is calculated by computing the reduction in variance of the target (class) variable due to the variable via a sensitivity analysis. The average variable variance reduction (importance) over all ALSFRS items, or that for each item separately, determines ranking/order for the importance of the variables by which they can be optimally selected for classification. Variable importance can be computed also by other measures, such as the Gini impurity index.

Finally, the normalized sensitivities of the variables (V Li) are ranked, determining an order of importance for the variables by which they can be optimally selected for classification.

Figure 9:
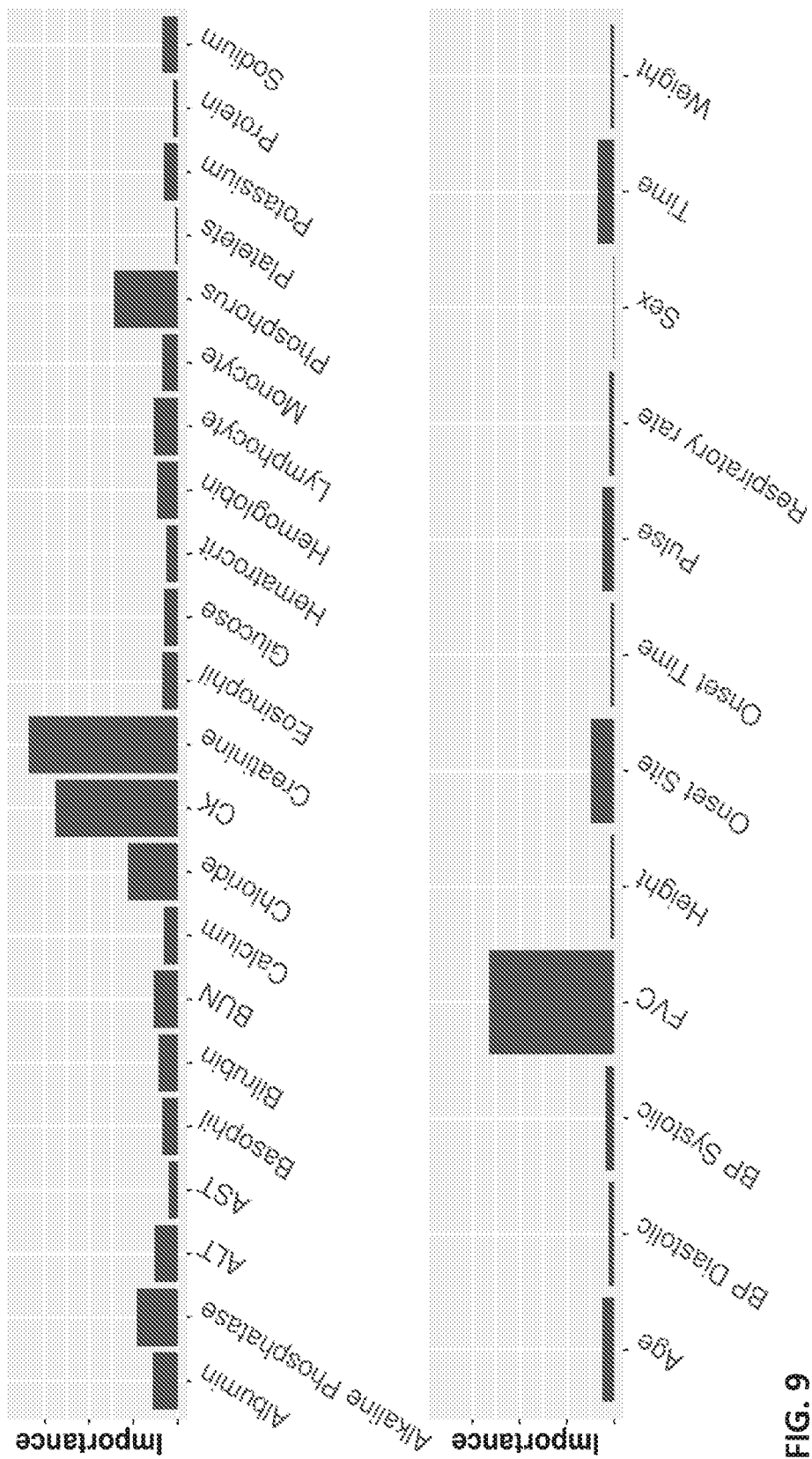
FIG. 9 depicts average classifier-based importance of lab test and non-lab test variables averaged over the ten ALSFRS items in accordance with an embodiment.

FIG. 9 depicts importance of lab test (top) and non-lab test (bottom) variables based on the DTs and averaged over the ten ALSFRS items measured in two clinic visits. "Time" is a measure of the time values documented from the beginning of a clinical trial and BP represents blood pressure.

Specifically, FIG. 9 displays non-lab test variables that proved important: FVC, Onset Site, and Time, which are also known to be important from previous research. The most important of these is FVC, which is a symptom of the disease as well as a variable. While non-lab variables may be important with regard to prediction, they are of less interest when exploring underlying mechanisms of the disease and risk factors. Therefore, in this study, we were more interested in analyzing lab test variables.

Furthermore, FIG. 9 shows that among the lab test variables, there are a number that stand out, namely creatinine (a naturally-occurring nitrogenous organic acid involved in adenosine triphosphate (ATP) production), CK (creatine kinase, an enzyme found e.g., in skeletal muscles), chloride, phosphorus, and alkaline phosphatase. Creatinine, CK, and phosphorus have recently been mentioned in other studies as being related to the disease (creatinine and CK were also found to correlate to each other). Surprisingly, the rest of these variables are identified as being related to the disease. Advantageously, variable importance is shown to be important with relation to a specific ALSFRS item (below), besides being important when averaged over the ten values.

Figure 10A:
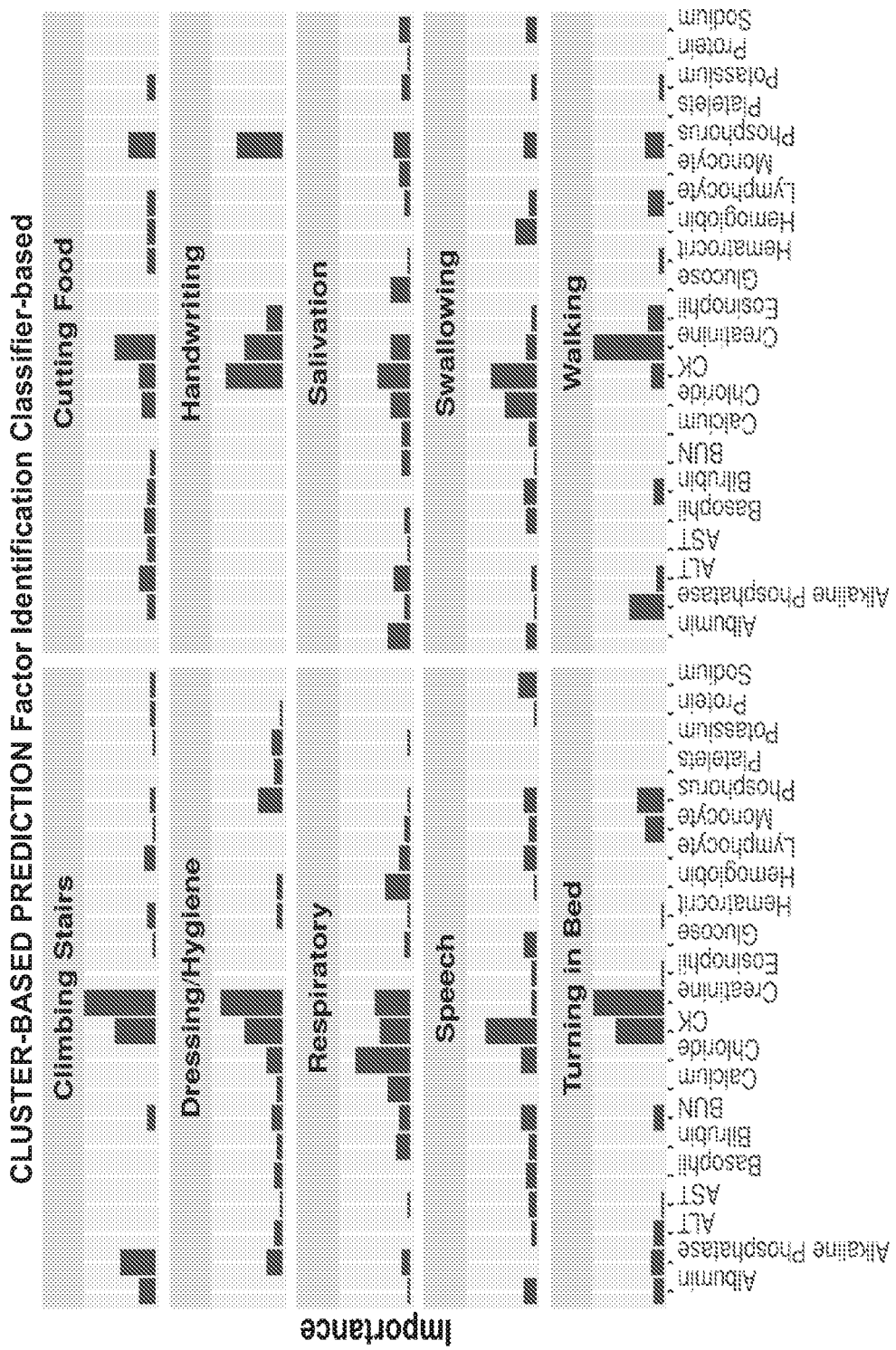
FIG. 10A depicts classifier-based importance of lab test variables for each of the ten ALSFRS items, in accordance with an embodiment.

FIG. 10A provides a visual depiction of how different aspects of the disease (as represented by the separate ALSFRS items) relate differently to the lab test variables, thereby confirming the effectiveness of this new approach of treating different aspects of the disease separately, rather than as a sum (or average) over all of the functions, as done conventionally.

Specifically, FIG. 10A shows that CK is the most or second most important factor for most ALSFRS items, and especially for bulbar functions (Swallowing, Speech, and Salivation), but also for full body functions (Dressing/Hygiene and Turning in Bed) and other functions (e.g., Handwriting and Climbing Stairs). Creatinine is the most important variable for functions that are related to major muscles of the lower body, such as Walking and Climbing Stairs, or in full body functions, such as Dressing/Hygiene and Turning in Bed. Chloride is the most important variable for the Respiratory function (a function that plays an extremely important role in disease progression), and the second most important variable for Swallowing.

FIG. 10A also demonstrates that the contribution to the average importance of phosphorus that is shown in FIG. 9 mainly involves upper and full body functions: Cutting Food, Handwriting, Dressing/Hygiene, and Turning in Bed, and alkaline phosphatase mainly relates to Walking and Climbing Stairs.

Figure 10B:
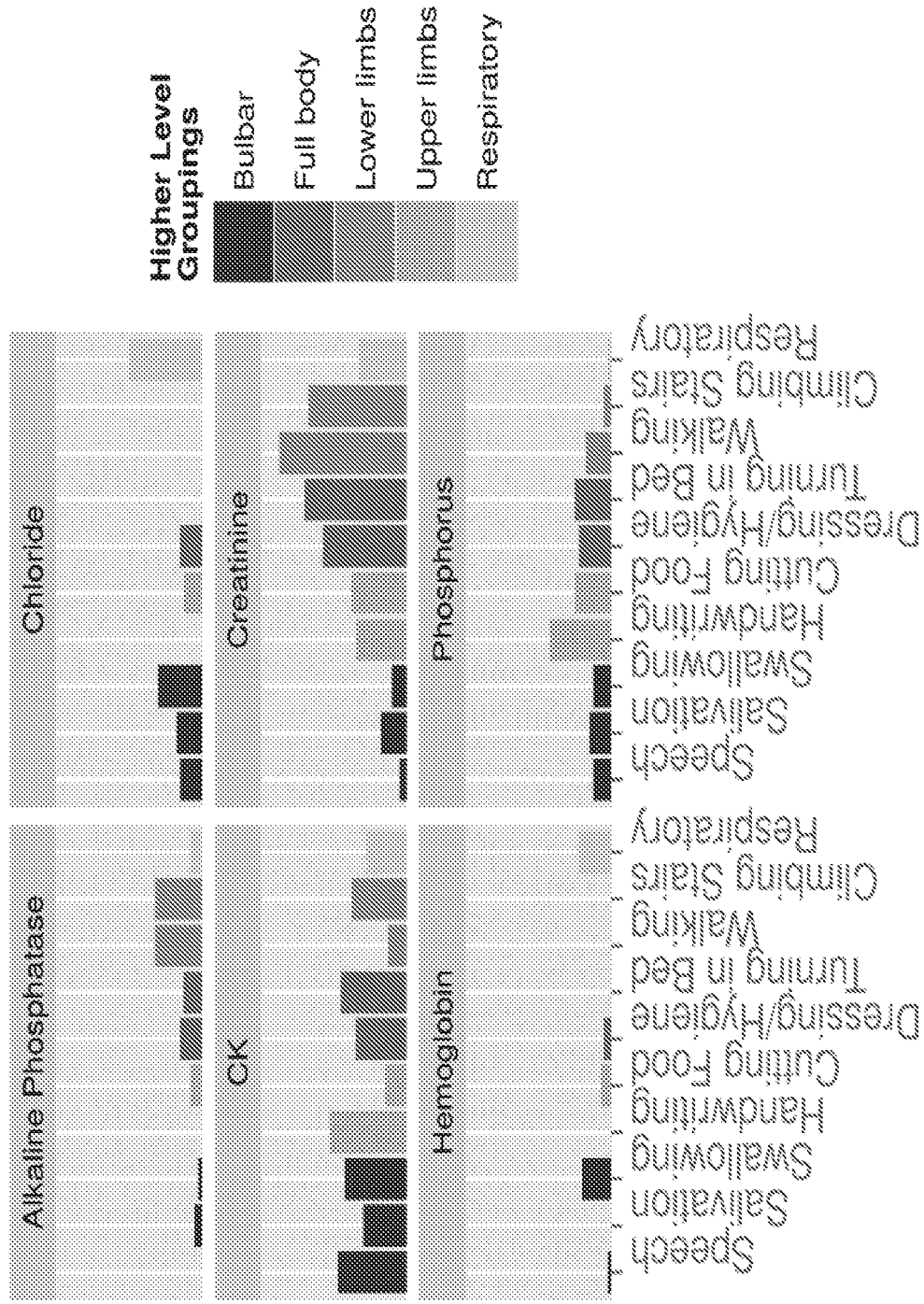
FIG. 10B depicts classifier-based importance of significant lab test variables for the ten ALSFRS items, arranged in the five body function groups, in accordance with an embodiment.

FIG. 10B depicts variable importance of significant lab test variables for the body function ALSFRS groups. The importance noticed for individual ALSFRS items is repeated for all or most of the group items.

Step 234 is further accomplished as part of process 215. For the prediction of disease progression rate, factor identification is repeated for each of a plurality of clusters derived in step 220. The aim is identifying the most predictive set of features for each cluster. The patient population was bootstrapped 1,000 times. For each sample, a random forest (RF), which is a state-of-the-art classifier, was trained in each cluster separately to predict the total ALSFRS rate in months 4-12 using only features from months 1-3 for this cluster patients. The clinical motivation is to enable prediction of a patient progression rate to the future using only their physiological and lab test variables in the first clinic meeting. For each such RF (cluster), feature importance were evaluated using measures of decrease in accuracy and node impurity, although other measures described above are appropriate as well, when the initial feature set included or excluded ALSFRS items as features. When the ALSFRS items were included in the potential feature set, also included were the values for the ALSFRS groups besides those for the items themselves. This was to allow the models to select meaningful summations of the separate ALSFRS items in case these summations are more informative than the separate items. Finally, average values of importance were calculated for each feature and cluster over the entire bootstrapping procedure and used to rank the features.

TABLE 4

Five most predictive features for each cluster including ALSFRS items

| Feature rank | Cluster 1 | Cluster 2 | Cluster 3 | Cluster 4 |
|---|---|---|---|---|
| 1 | onset delta | onset delta | Lower limbs | Full body |
| 2 | FVC | Salivation | ALSFRS (total) | CK |
| 3 | pulse | Alkal. Phos. | weight | FVC |
| 4 | BP diastolic | FVC | Salivation | phosphorus |
| 5 | ALSFRS (total) | potassium | Respiratory | Dressing/ hygiene |

TABLE 5

Five most predictive features for each cluster excluding ALSFRS items.

| Feature rank | Cluster 1 | Cluster 2 | Cluster 3 | Cluster 4 |
|---|---|---|---|---|
| 1 | chloride | gender | albumin | albumin |
| 2 | basophils | phosphorus | creatinine | phosphorus |
| 3 | BP diastolic | chloride | BP diastolic | BP diastolic |
| 4 | albumin | FVC | Alkal. Phos. | chloride |
| 5 | creatinine | creatinine | BP systolic | BP systolic |

Tables 4 and 5 show the five highest ranked features for each cluster including and excluding ALSFRS items, respectively. Table 4 shows that e.g, forced vital capacity (FVC) and onset delta (number of days before a clinic visit and since a patient reported initial disease symptoms) are prominent features in the presence of the ALSFRS items, but not so prominent without them. This could imply that they have meaningful interactions with the ALSFRS items that the models picked up on. While only one or two ALSFRS items or groups are dominant in clusters 1, 2, and 4, four of the five most predictive features of cluster 3 are ALSFRS-based, perhaps implying the increased importance of functionality measures in representing fast progressors (cluster 3 in Table 2). Further shown in Table 5 is the lab test and physiological variables played a much more important part in prediction in the absence of the ALSFRS items (see e.g., the prominence of the blood pressure (BP) variables and of chloride, albumin, and creatinine). This again makes sense, as without direct access to the disease state, the models must make use of physiological and lab test variables as proxies.

Tables 4 and 5 show that each of the clusters have different features that are most predictive for it. Some features appear as important for a number of clusters (notably, onset delta and FVC in Table 4, and BP, chloride, albumin, and creatinine in Table 5), but others, such as potassium, CK, and other lab test variables seem to be most significant for only one cluster each. This further demonstrates the value of patient clustering and identification of important features for each cluster separately.

Casual-Based Factor Identification

In step 235, integrated system 100 also employs causal-based factor identification implemented through Bayesian network classification in step 236 to perform Markov blanket-based (MB) feature selection in step 237.

Specifically, in regards to step 236, Bayesian networks (BNs) use a graph-based representation as the basis for compactly encoding a complex distribution over high-dimensional spaces. In this graphical representation, nodes correspond to the variables in the problem domain, and the edges correspond to direct probabilistic interactions between the variables. BNs have a number of inherent advantages over other models: 1) they allow for the manifestation and visualization of higher level interactions among variables; 2) when combined with Bayesian statistical techniques, they allow incorporation of prior domain knowledge, which is a valuable asset especially in medical domains; and 3) they compactly and intuitively encode knowledge, and are thus an excellent tool for knowledge extraction and representation.

BNs are used to explore the mechanisms underlying ALS and its progression. Structure-learning techniques are employed to learn the graph architecture directly from the data. This facilitates further exposing relationships of the physiological and lab test variables, among themselves and with the disease state. For structure learning, algorithm called risk minimization by cross validation (RMCV) is employed. While most algorithms for BN structure learning attempt to learn the graph structure from the data using some scoring function that is typically based on the likelihood of all graph variables given the data, the RMCV algorithm searches for the graph that maximizes the prediction accuracy using the class variable. Such an approach fits this domain very well, since it employs a graph emphasizing variable relationships that have to do with the prediction of disease state, and not generally with the entire variable set. This approach, and maximizing the prediction accuracy of the learned structure with respect to disease state, advantageously focuses on variables influential to ALS, rather than attempting to maximize the likelihood for the entire variable set as done in conventional systems. Furthermore, by using RMCV, the potential benefit of the BNs is increased, which are usually used only in knowledge representation, by enabling their use for predictive purposes as well as for knowledge representation and explanation. After discretizing continuous variables in the database (RMCVs, as most BNs, work on discrete variables) using the minimum description length supervised discretization algorithm, a BN is learned from the data for each ALSFRS item using the RMCV algorithm. The RMCV search is initialized with an empty graph.

Regarding step 237, analyses of the supervised classification models have helped to pinpoint important physiological and lab test variables, and map them to different aspects of the disease. However, this analysis is limited in that interactions between these variables or understanding of context and flow of influence within the models is invisible. In contrast, BNs allow modelling the problem in such a way that exposes higher level interactions and relationships between variables, and between them and the target variable. To this end, BNs learned from the data using the RMCV algorithm; one network is employed for each of the ALSFRS items. Using the RMCV algorithm while defining the class variable to be the ALSFRS item restricts the learning process to concentrate on relationships and interactions that are important with respect to the disease state itself. The RMCV algorithm is initialized using only variables measured in the last clinic visit.

Figure 11A:
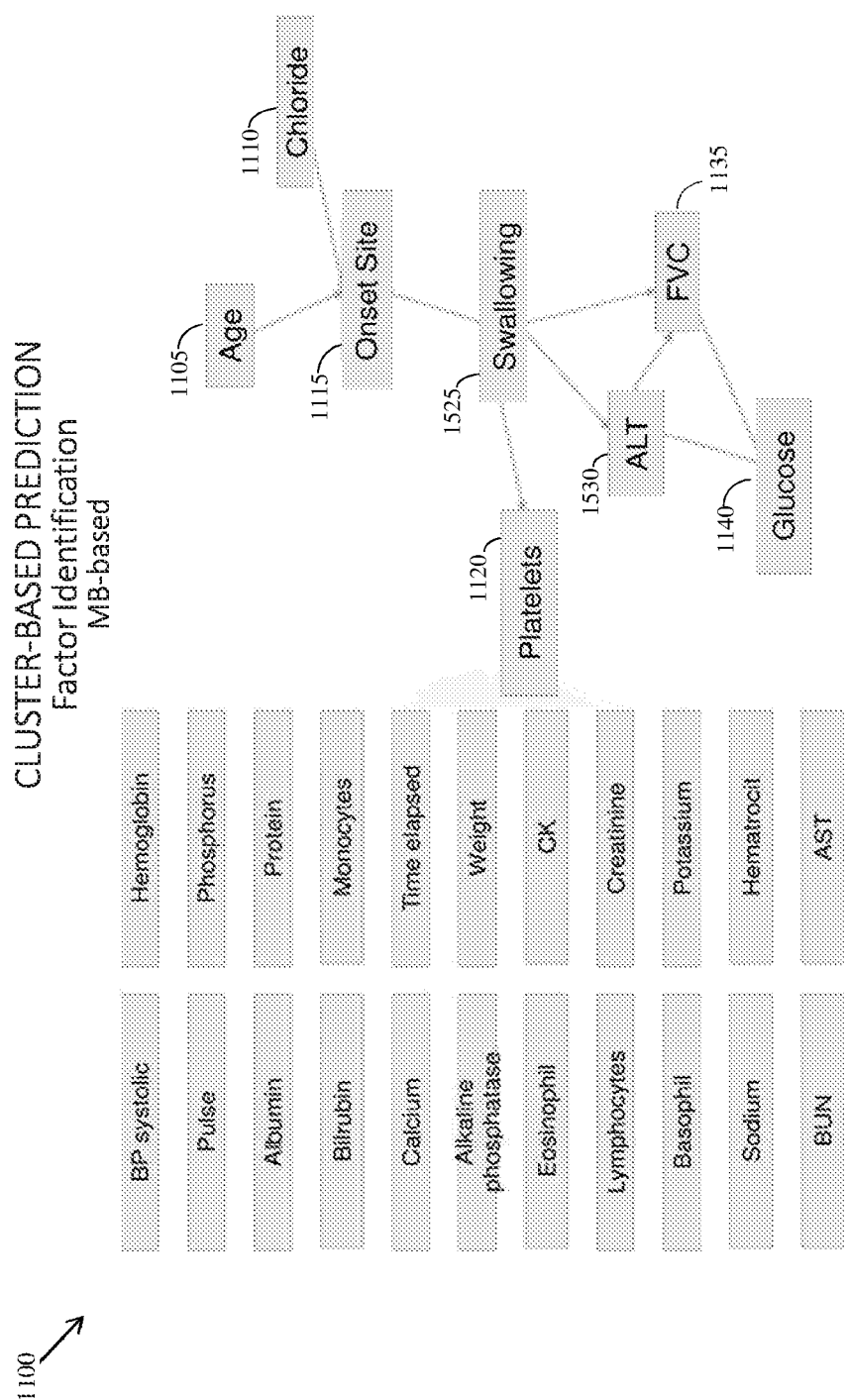
FIG. 11A is a graph for the Swallowing ALSFRS item showing unconnected variables and a Markov Blanket (MB) for Swallowing, in accordance with an embodiment.

FIG. 11A shows a complete BN graph for the ALSFRS item Swallowing 1525.

Specifically, FIG. 11A A displays the entire variable (node) set, but only relationships and connections that were important with respect to the class variable (Swallowing) 1525 were learned, where unimportant variables are not connected to the graph. This is another advantage of the RMCV algorithm, in that structure learning also applies naturally to feature selection that is augmented towards prediction. After learning is complete, only the MB for the class variable is learned as only variables in the MB can affect and be affected by the class variable.

The MB demonstrates another advantage of BNs, which is their interpretability. Based on such graphs, ALS clinicians are able to explain connections they see in the BN from their own knowledge, even though these sometimes may not have been known or thought of in advance. Alternatively, medical knowledge can validate the BN model. For example, the connection seen in the MB between Swallowing 1525 and Onset Site 1115 is well known, as almost all bulbar-onset patients develop excessive drooling due to difficulty in swallowing saliva (see the edge from Swallowing to Onset Site). FVC 1135, which is a measure of the respiratory system, is also affected by the ability to swallow, and difficulties in swallowing worsen the ability of the respiratory system (See the directed edge from Swallowing 1525 to FVC 1135 in FIG. 11AA). Low glucose levels 1140 in the blood may be caused by difficulties in swallowing (low food intake), and these low levels may cause harm to the breathing muscles, which decreases FVC 1135 (see directed edge glucose 1140→FVC 1135). While the connection Glucose 1140→ALT (alanine aminotransferase) 1530 may represent the Glucose-Alanine cycle between the muscles and the liver, the connection Swallowing 1525→ALT 1530←Glucose 1140 represents that when the value of ALT 1530 is known, Swallowing 1525 and Glucose 1140 are (conditionally on ALT 1530) dependent. Note also that elevated levels of ALT 1530 in the blood that are measured with elevated levels of CK—that although is not part of Swallowing's MB is an important variable of Swallowing 1525 (see FIG. 10A)—are a major indicator of ALS, as both enzymes are included among the muscle enzymes. In addition, studies show that Age 1105 does not affect ALS, despite the higher frequency of bulbar-onset cases among older women (see directed edge Age 1105→Onset Site 1115), but the complex relationships between age and bulbar onset remain to be clarified. Furthermore, it is possible that the diet of the bulbar-onset patients, having difficulties with swallowing, and thus moving to tube feeding, is not balanced with respect to chloride (see the edge Chloride 1110→Onset site 1115).

Figure 11B:
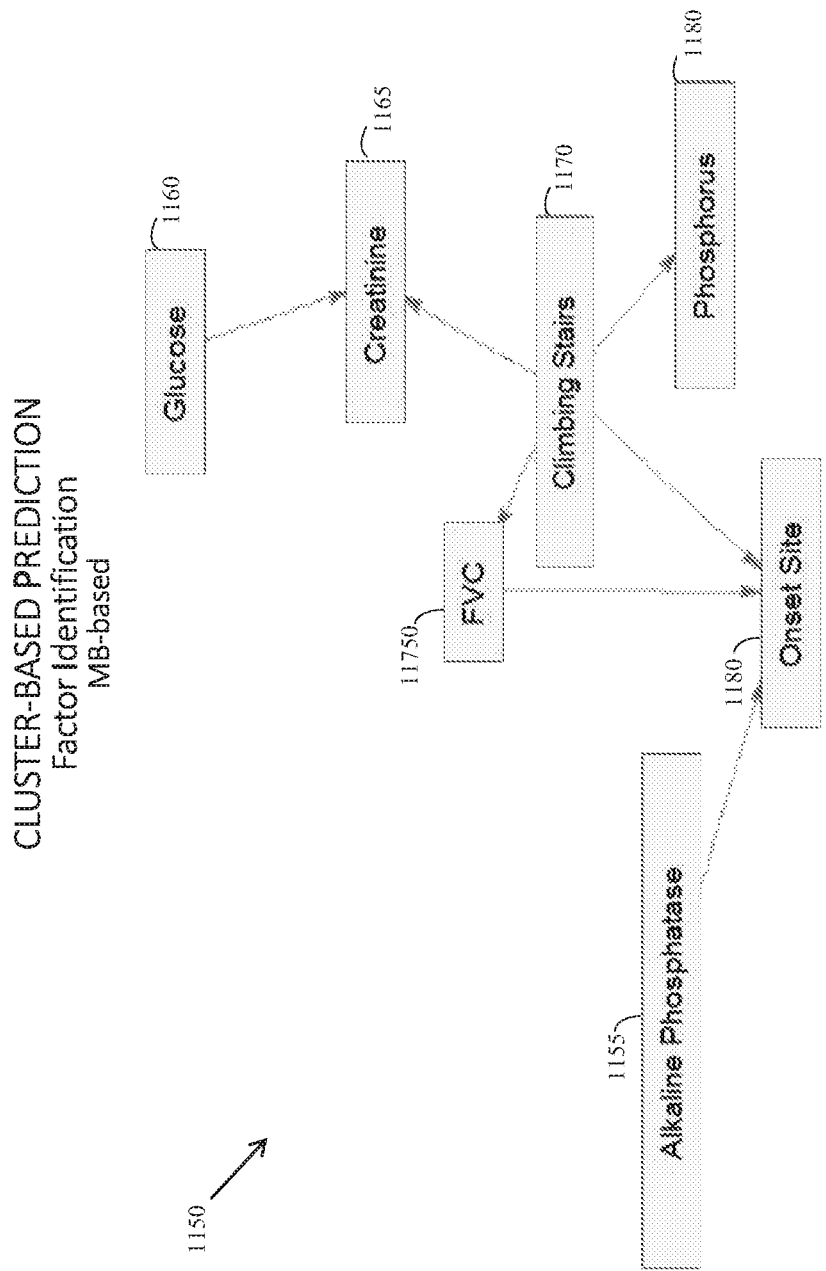
FIG. 11B is a Markov blanket for the Climbing Stairs ALSFRS item, in accordance with an embodiment.

Similarly, FIG. 11B shows the learned MB for Climbing Stairs 1170, demonstrating interesting relations among the MB's variables. FIG. 11B shows relations of patient functioning ability in climbing stairs 1170 with four lab test results, FVC 11750, and Onset Site 1180. Also, these relations can mostly be explained medically. Briefly, as glucose 1160 and creatinine 1165 are important for and related to energy metabolism, they are connected by an edge. Glucose 1160 is the main energy source of muscles and is needed to create and maintain muscle activity, while serum creatinine diminishes with disease progression following a decrease in the muscle mass. Note that if the muscle mass was measured (or estimated) in the clinic visits and introduced into the model, more interesting connections among Glucose 1160, Creatinine 1165, Climbing Stairs 1170, and muscle mass could have been identified. Phosphorus 1180 changes are related to muscle weakness that is experienced while climbing stairs. High alkaline phosphatase 1155 values are found in people with low motor performance, due to physical disability (e.g., in climbing stairs), and in our case, these people may be limb-onset patients (Onset Site 1180=limb). Respiratory insufficiency, which is reflected in low values of FVC 11750, makes any physical activity, e.g., climbing stairs 1170, much more difficult. Note again that if information about muscle condition could be brought into the model through some "muscle variables", these variables could be found related to both the abilities to climb stairs and to breath (affecting FVC 11750).

Analysis of Factor Value Combinations

Based on the MBs, distributions over value combinations of important variables included in the MB with respect to the different aspects of the disease (ALSFRS items) are analyzed. If the MBs were small enough, combinations for all variables in the MB of each item could be analyzed. However, since nearly all BNs yielded moderate-sized MBs, which are intractable to analyze in this manner, incorporated knowledge about variable importance (FIG. 10A) helped derive sets of four important variables selected from the MB for each ALSFRS item. Table 6 below shows these four-variable sets for the ten ALSFRS items.

Based on different combinations of the important variables for each item, the patient population can be divided into two groups: those with an ALSFRS value of zero or one during the last clinic visit ("severe" patients), and those with an ALSFRS value of 3 or 4 ("mild" patients). For each ALSFRS item, the frequencies of all possible combinations of the four variables for each patient group are computed.

TABLE 6

Four important variables selected from the MB for each ALSFRS item

| Function | Variable 1 | Variable 2 | Variable 3 | Variable 4 |
|---|---|---|---|---|
| Speech | FVC | Onset site | CK | chloride |
| Salivation | FVC | Onset site | creatinine | potassium |
| Swallowing | FVC | Onset site | ALT | chloride |
| Handwriting | FVC | Onset site | CK | potassium |
| Cutting Food | FVC | CK | chloride | phosphorus |
| Dressing/Hygiene | FVC | Onset site | potassium | CK |
| Turning in Bed | FVC | Onset site | creatinine | potassium |
| Walking | FVC | alkaline phosphatase | creatinine | CK |
| Climbing Stairs | FVC | alkaline phosphatase | creatinine | phosphorus |
| Respiratory | FVC | CK | hemoglobin | Potassium |

Figure 12:
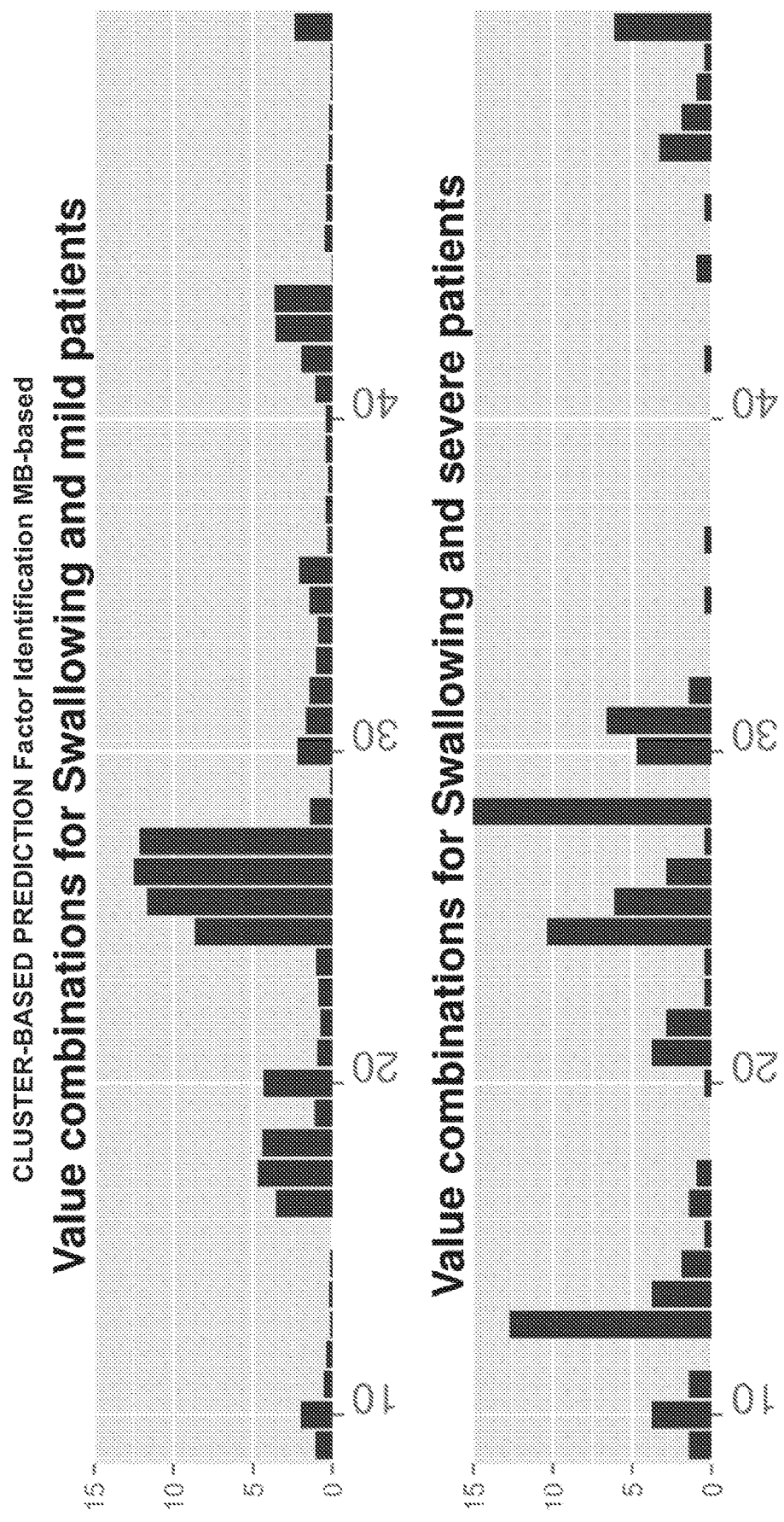
FIG. 12 depicts distributions over all 64 possible value combinations of four MB-based important variables for Swallowing for mild and severe patients, depicted in the top and bottom charts, respectively, in accordance with an embodiment.

FIG. 12 depicts distributions over all 64 possible value combinations of the four important variables for Swallowing for mild patients and severe patients, depicted in the top and bottom charts, respectively, demonstrating significant differences between severe and mild patients. Some of the value combinations are very frequent for mild patients while are less frequent or even rare for severe patients and vice versa. Graphs such as that in FIG. 12 are derived for all the ALSFRS items.

The six most frequent value combinations for each group of patients for every ALSFRS item were inspected. Table 7 shows these combinations for the four most important variables for Swallowing (Table 6), together with the frequencies of severe and mild patients for each combination. Combinations 1-6 are the most frequent for severe patients, while combinations 3 and 6-10 are the most frequent for mild patients (note that combinations 3 and 6 are shared by the two patient groups). Table 7 indicates differences between mild and severe patients with respect to the value combination frequencies. Tables such as Table 7 and graphs such as that in FIG. 12 were derived for all ALSFRS items.

TABLE 7

Six most frequent value combinations for severe and mild patients for Swallowing

|  | FVC | Onset Site | ALT | Chloride | Severe patients (%) | Mild patients (%) |
|---|---|---|---|---|---|---|
| 1 | low | bulbar | high | normal | 16.04 | 1.40 |
| 2 | low | bulbar | high | low | 12.74 | 0.14 |
| 3 | low | limb | high | normal | 10.38 | 8.64 |
| 4 | moderate-high | bulbar | high | normal | 6.60 | 1.68 |
| 5 | low | limb | high | low | 6.13 | 2.38 |
| 6 | moderate-low | limb | high | normal | 6.13 | 11.67 |
| 7 | moderate-high | limb | high | normal | 2.83 | 12.51 |
| 8 | high | limb | high | normal | 0.47 | 12.14 |
| 9 | moderate-low | limb | normal | normal | 0.94 | 4.72 |
| 10 | moderate-high | limb | normal | normal | 0.00 | 4.44 |

It is shown from Table 7 and FIG. 12 that the combinations are different between the two groups of patients. For example, the combinations for which FVC=low (including combination 4 for which FVC=moderate-high) and ALT=high, regardless of the values of Onset Site and Chloride, are typical to severe patients, sometimes in up to an order or two of magnitude more than for mild patients. Combinations 6-10 and 3 with Onset Site=limb, Chloride=normal, and FVC=not low (except for combination 3), regardless of the value of ALT, are prevalent in mild patients even in up to two orders of magnitude more than for severe patients. The two combinations that are frequent for both patient groups (i.e., 3 and 6) have frequencies that are not very different between these groups. It might be that the second patient group (limb-onset patients having FVC values that are not low) is of patients in the database that are in their early stages of disease and thus, with high probability, are mild patients, whereas the first group (patients having low FVC values) is of patients in their late stages of disease, and thus, with high probability, are severe patients.

This type of analysis of the distributions of value combinations of important variables advantageously has potential to expose and explain interesting and possibly meaningful underlying mechanisms of ALS unknown in conventional predictions systems.

values of the last visit recorded for a patient based on features from both the first and last visit recorded for a patient. The algorithms are: Cumulative Link Models (CLMs), Ordinal Decision Trees (ODTs), and Cumulative Probability Trees (CPTs). They all suit the ordinal nature of the ALSFRS value. Other algorithms that account for it are suitable as well. Table 8 shows that the average mean absolute error (MAE) is between ≈0.6 and ≈2 in points of ALSFRS scores depending on the model, setting, and item. Statistical testing reveals that there is no significant difference between the performance of CLM and ODT (p-value≈0.39 for a paired student's t-Test) in the first and second settings and both err in less than a point in most cases. In the predictive setting (setting 3), the difference between them is significant (p-value~0.012) in favor of ODT. However, in all three settings, there are significant differences between CLM and CPT (p-value 2.22e−06), CLM and RF (p-value 1.88e−06), ODT and CPT (p-value 2.41e−08), and ODT and RF (p-value 1.13e−05). The difference between RF and CPT is significant (p-value~0:026) in favor of CPT for all three settings, but depending on how we account for multiple testing might not be considered significant.

Figure 13:
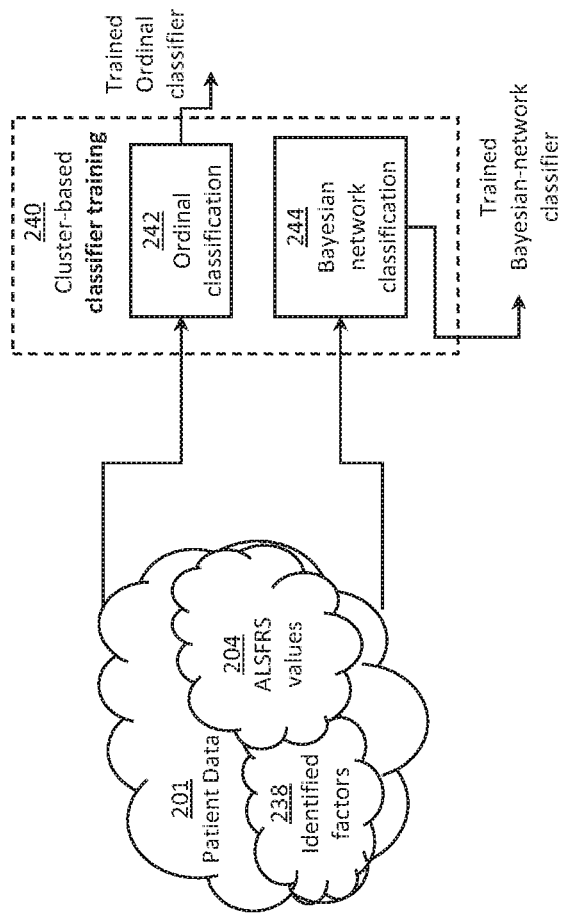
FIG. 13 depicts the processing steps implementing the cluster-based classifier training step 240 of FIG. 2C, in accordance with an embodiment.

FIG. 13 depicts the processing steps implementing the cluster-based classifier training step 240 of FIG. 2, in accordance with an embodiment;

TABLE 8

MAE for three settings, four prediction models, and ten ALS items (bold is best over algorithms)

| | Alg. | Speech | Respiratory | Salivation | Swallowing | Handwriting | Cutting Food | Dressing/ Hygiene | Turning in Bed | Walking | Climbing Stairs |
|---|---|---|---|---|---|---|---|---|---|---|---|
| Last visit | CLM | 0.78 | 0.67 | 0.81 | 0.76 | 1.07 | 1.05 | 0.82 | 0.85 | 0.80 | 0.74 |
| | ODT | 0.79 | 0.66 | 0.78 | 0.77 | 1.02 | 0.99 | 0.84 | 0.89 | 0.80 | 0.73 |
| | CPT | 1.77 | 2.11 | 2.02 | 2.00 | 1.46 | 1.25 | 1.13 | 1.33 | 1.20 | 0.91 |
| | RF | 1.37 | 1.42 | 1.57 | 1.45 | 1.44 | 1.23 | 1.09 | 1.22 | 1.14 | 1.02 |
| Both visits | CLM | 0.71 | 0.62 | 0.76 | 0.68 | 1.06 | 1.02 | 0.81 | 0.84 | 0.77 | 0.76 |
| | ODT | 0.78 | 0.83 | 0.79 | 0.74 | 1.01 | 1.00 | 0.85 | 0.89 | 0.77 | 0.77 |
| | CPT | 1.76 | 2.13 | 2.02 | 2.00 | 1.47 | 1.29 | 1.12 | 1.39 | 1.24 | 0.94 |
| | RF | 1.39 | 1.39 | 1.61 | 1.46 | 1.45 | 1.20 | 1.10 | 1.23 | 1.14 | 1.01 |
| First visit | CLM | 1.55 | 0.89 | 1.15 | 1.20 | 1.42 | 1.50 | 1.37 | 1.39 | 0.85 | 0.95 |
| | ODT | 1.16 | 0.77 | 1.01 | 0.99 | 1.22 | 1.15 | 1.02 | 1.10 | 0.85 | 0.96 |
| | CPT | 1.77 | 2.11 | 2.01 | 1.96 | 1.45 | 1.52 | 1.41 | 1.30 | 1.17 | 0.96 |
| | RF | 2.18 | 1.61 | 2.06 | 2.03 | 1.84 | 1.26 | 1.20 | 1.60 | 1.34 | 0.99 |

This concludes the analysis of the stratification concept and a learned clustering scheme over the entire patient population.

Classifier Training

In step 240, a cluster-based classification embodiment is implemented in a first variant embodiment through an ordinal classifier and a second variant embodiment is implemented through a Bayesian network classifier.

Specifically, this step relates to predicting the progression pattern of a new (previously unseen) patient (i.e., by assigning them to a cluster), and deals with incorporating this information into a system designed to predict a patient's total future ALSFRS rate.

Table 8 details MAE results for three settings and three ordinal prediction models in comparison to a RF to see if accounting for the ordinal nature of the target variable can improve performance. The settings are: "Last visit"—predicting ALSFRS values of the last visit recorded for a patient based on features (e.g., vital signs and lab test results) from that visit; "First visit"—predicting ALSFRS values of the last visit recorded for a patient based on features from the first visit recorded; and "Both visits"—predicting ALSFRS Table 8 shows that accounting for the ordinal nature of the problem clearly improves prediction performance, and CLM and ODT significantly outperform the RF classifier, which can typically be expected to achieve performance at least as good as a tree model. The table also shows that, as expected, the predictive setting 3 ("First") poses more difficulty than settings 1 ("Last") and 2 ("Both"); all of the models (with the exception of CPT) perform significantly better in settings 1 and 2 than in 3. Further investigation reveals that the CPTs are simply predicting the class with the highest a priori probability, and therefore performance is not improved between the settings for this model. Finally, using CPT models as a baseline, we can see that all the other models are able to improve prediction performance as measured by MAE significantly over a model that simply predicts the class with the highest a priori probability.

In step 244, Bayesian networks are trained for classification using the RMCV algorithm (as was explained for steps 236 and 237). Actually, when training is complete, the Bayesian network classifier is ready for: factor identification based on its learned MB (step 237) and classification of new patients (step 244).

Classification which is not ordinal does not take into account the ordinal nature of the target function, and thus "small" errors and "large" errors affect training similarly. It is common to demonstrate errors in a confusion matrix, where each of its entries measures the number (or percentage) of data points for which true class x was predicted as y for every x and y. Example for confusion matrices is given in FIG. 14, showing matrices for each of the ALSFRS items when predicting disease state using only information from the first clinic visit.

However, in ordinal classification, the classifier is penalized more for making large errors (say, predicting an individual ALSFRS item as 3, where it is actually 1) than for making small errors (say, predicting an individual ALSFRS item as 2, where it is actually 1). Such a paradigm suits the ordinal ALSFRS nature better, and then it is not the classification accuracy that measures classifier performance but the mean absolute error, which is the sum of absolute difference between predictions and true values.

In step 250, a new patient is assigned to a best fitting cluster using data from early stages of the disease. We assign a new patient to the cluster that best matches a patient's future disease progression. To this end, some of the patients in the database are set aside to use as test (future) patients, models are trained using the rest of the patients, including learning a clustering scheme, and then evaluated on the test patients. Training models to predict a progression pattern for a test patient by assigning this patient to their most representative cluster is also performed using training patients. Not including knowledge of test patients in the training phase reduces the bias in performance estimations. In predicting a patient's future total ASLFRS rate, a prediction model is trained for each cluster, and for each new patient, the model associated with the cluster the patient is assigned to is used, thereby tailoring prediction of progression to each specific patient individually. When assigning a future patient to a cluster, it is unknown beforehand which will be the most representative cluster for this patient, thus one cannot employ any of the feature representations we already found for the clusters.

Therefore, patient feature representation for cluster assignment cannot be cluster specific but entire-population-based. In order to regularize model complexity and reduce prediction variance, the models were limited to five predictive features, which were selected via a feature importance selection procedure as detailed above in the context of step 230 using a single RF for the entire population. This naturally yields a different set of most predictive features than those found when training models for cluster-specific patients. The features selected were onset delta, Speech (ALSFRS item), Dressing/Hygiene (ALSFRS item), Full body (sum of Turning in Bed and Dressing/Hygiene ALSFRS item), and FVC. For each of the dynamic features (i.e., features with multiple values recorded during the first three months), the minimal and maximal values as features were extracted. The static feature (onset delta) was included as is in the patient representation, establishing a feature set of nine features. There are three methods for the task of assigning a new patient to a cluster (i.e., predicting his future progression pattern):

Method 1: Learn a clustering scheme for the patients in the training set as in step 220. Then construct a population-based feature representation (using the above 9 features) for the patients in the training set (all clusters), and consider their cluster assignments as labels. Finally, train a model to classify the cluster assignment based on the features. This model will later be applied to future (test) patients to assign them a cluster.

Method 2: Train five separate regression models (using RFs) using the patients in the training set to map patient population-based feature representation to each of the five ALSFRS group rates. This creates for each patient a five-dimensional vector of rate predictions for the five groups. Next, learn a clustering scheme for the patients in the training set (using the true group rates) and compute the five dimensional cluster centroids. Finally, predict the five ALSFRS group rates for each test patient, and assign this patient to a cluster based on the minimum Euclidean distance between a vector of these predicted group rates and any of the cluster centroids, $$C_i = \operatorname*{argmin}_j \left\| \hat{Y}_i - A_j \right\|_2,$$

where $C_i$ is the cluster assignment for patient i, $\hat{Y}_i$ is the vector of predicted rates for test patient i, and $A_j$ is cluster centroid j (both $\hat{Y}_i$ and $A_j$ are five-dimensional).

Method 3: This method is similar to Method 2, except that instead of learning the clustering scheme around the true rates of the training set patients, learn a clustering scheme around the predicted rates of the training set. The motivation for this method is that the predicted rates contain a certain bias of the model predicting them, in that they differ from the true rates in a specific way due to the structure learned by the predictive model. To minimize this bias and the difference between the representation used to assign patients to a cluster and the representation used to learn the clustering scheme, the predicted rates of the training patients are used when learning the clustering scheme. In this fashion, the clustering scheme was learned over the same representation that would later be used to assign a test patient to one of these clusters, thus minimizing the bias mentioned above.

In all three methods, RFs were employed since they are very powerful and popular prediction models often used in tasks were the mapping from features to target variables is assumed to be non-linear and complex. The parameters were set for the RFs—namely the number of trees per forest and the number of variables sampled to consider per split in a tree—using K-fold cross validation (CV-K), with K=10.

Figure 15A:
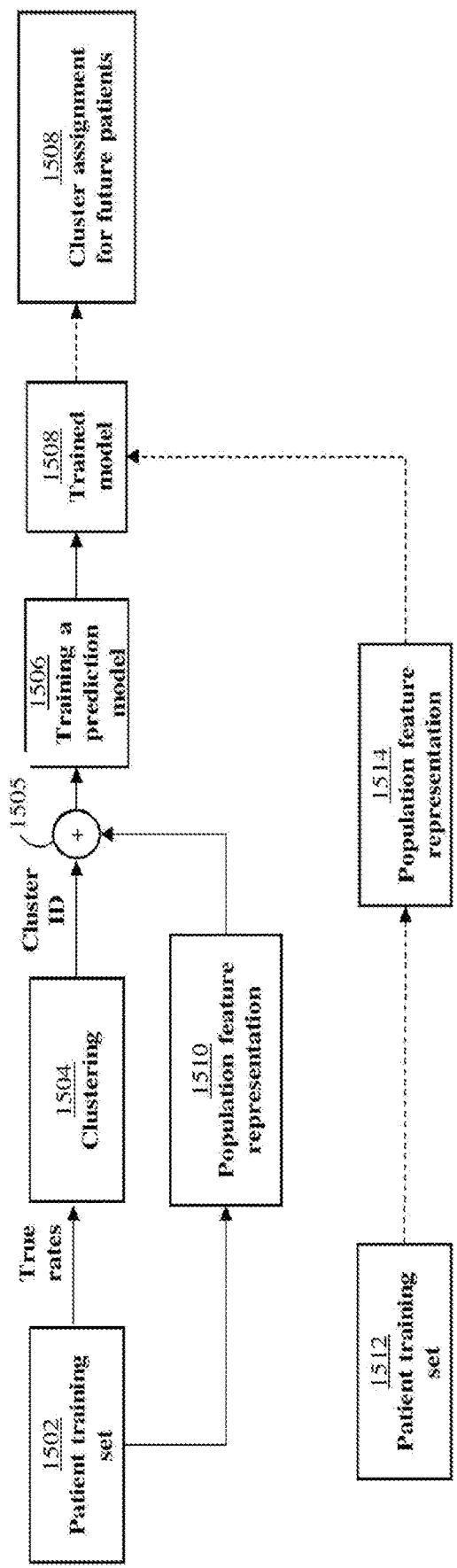
FIGS. 15A-15C depict three methods for assigning a new patient to a cluster for predicting his future progression pattern, in accordance with variant embodiments.
Figure 15B:
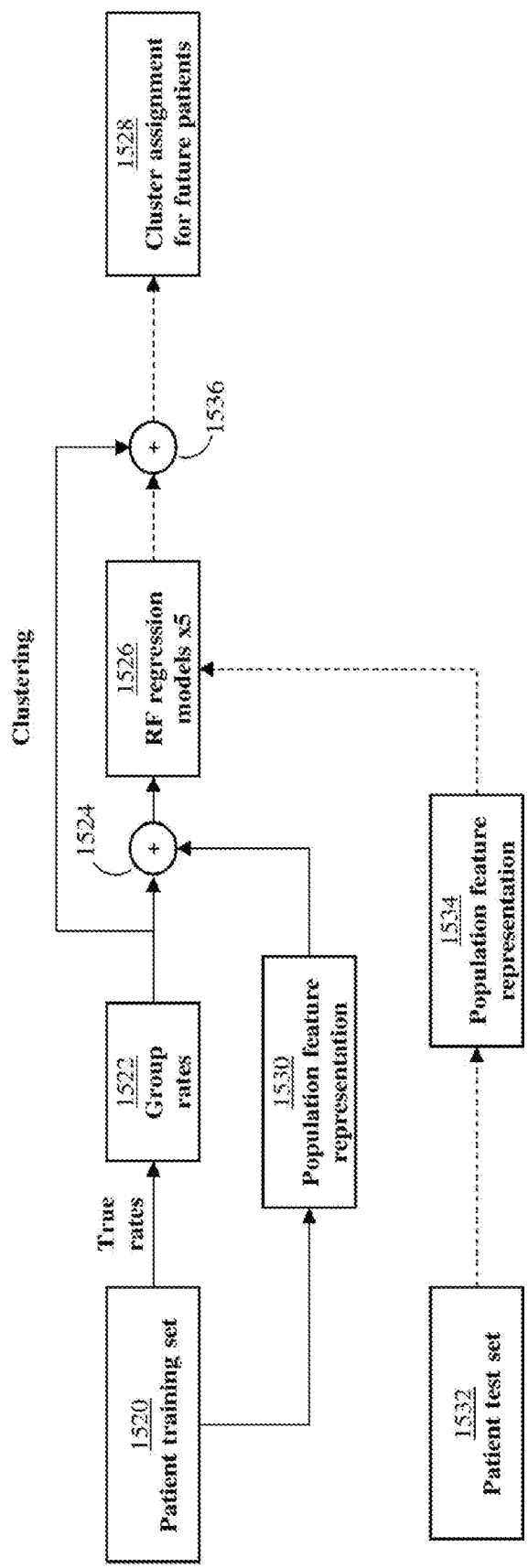
Figure 15C:
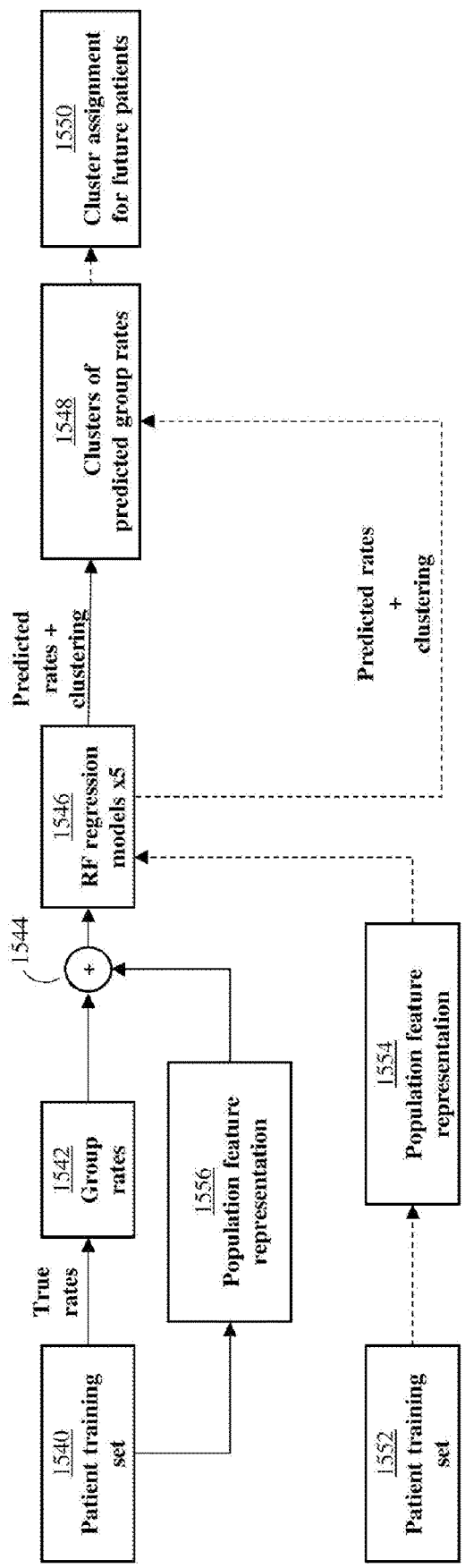

FIGS. 15A-15C depict methods 1-3 described above for assigning a future patient to a cluster. Dashed lines represent paths in the test phase.

In step 260 of FIG. 2C, the integrated system predicts a new patient's future disease progression rate. In this task, disease state is represented by the sum (total) of the ALSFRS items, and information from the first three months of a clinical trial are used to predict the rate of disease progression for the remainder of the first year. There are three settings for assimilating cluster-assignment information in such a prediction pipeline, and three methods of prediction, compared to a baseline model.

Figure 16A:
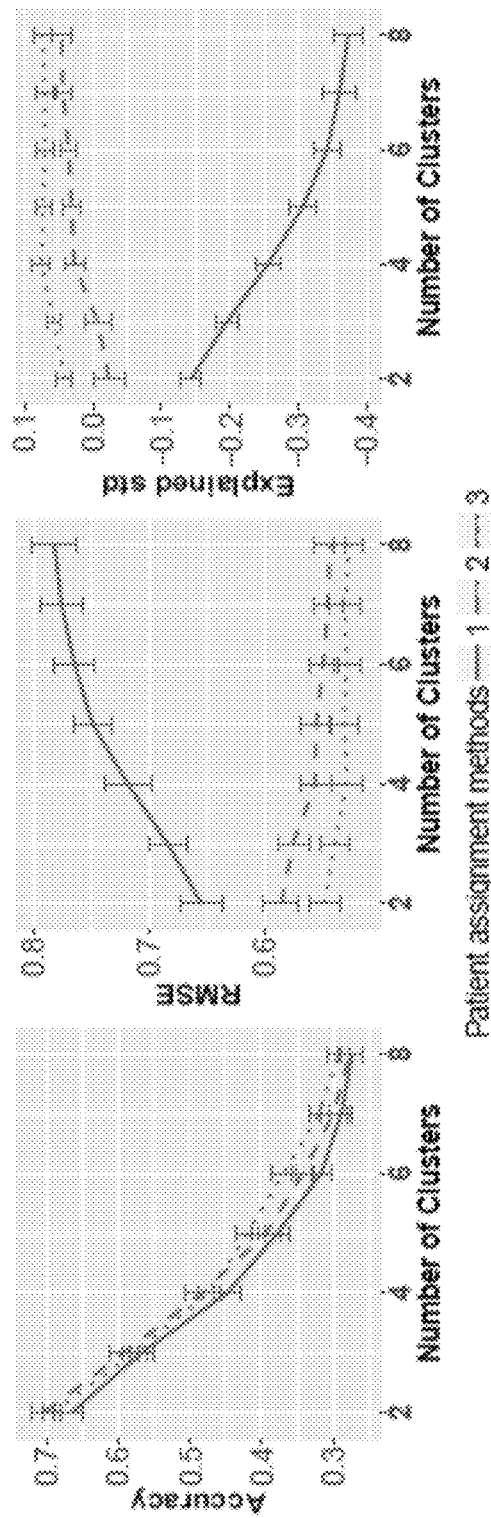
FIG. 16A depicts three model performance measures as a function of the number of clusters for the three assignment methods depicted in FIGS. 15A-15C.

Specifically, FIG. 16A depicts cluster-assignment accuracy, RMSE, and explained standard deviation as a function of the number of clusters for the three assignment methods depicted in FIGS. 15A-15C. The lines represent mean values, and the error bars are one standard deviation over the bootstrapping procedure.

Figure 16B:
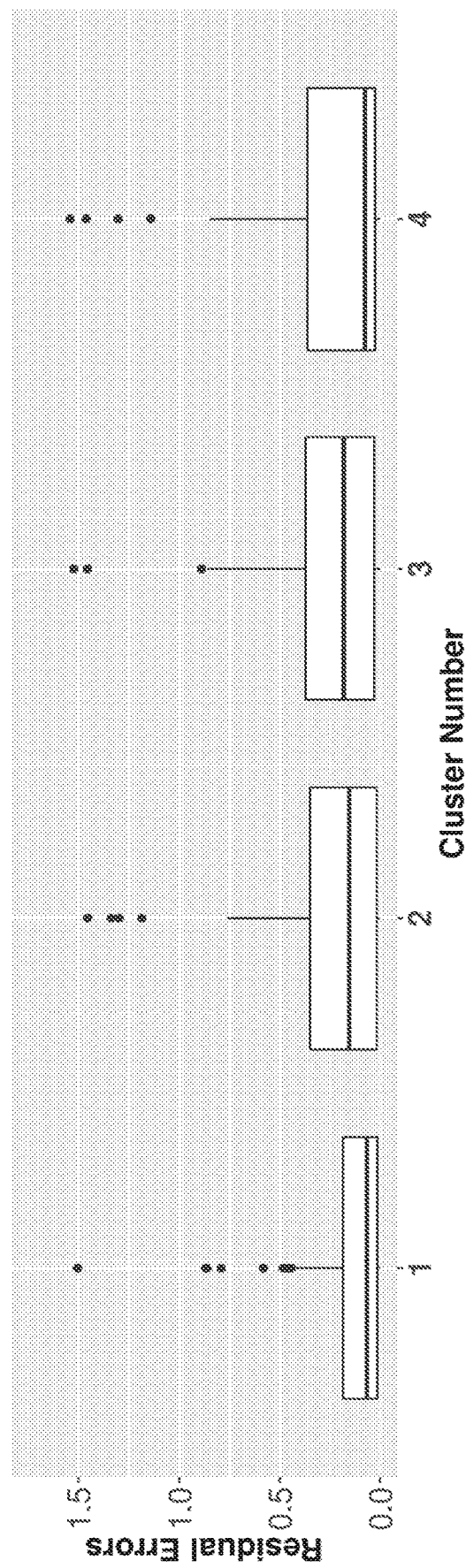
FIG. 16B depicts cluster-dependent prediction error box-plots for four patient clusters derived based on the performance measures in FIG. 16A.

FIG. 16B depicts cluster-dependent error boxplots for the assignment methods depicted in FIGS. 15A-15C.

Figure 16C:
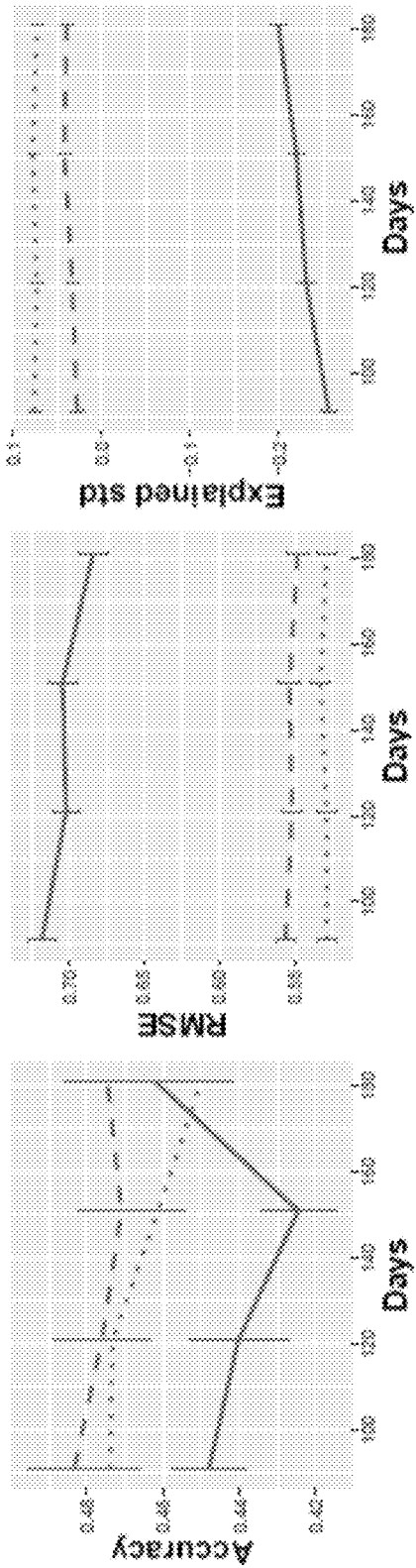
FIG. 16C depicts three model performance measures as a function of the number of days used for patient representation in the training set using four patient clusters for each of the three assignment methods depicted in FIGS. 15A-15C.

FIG. 16C shows three performance measures for the quality of prediction of disease state (represented by the total ALSFRS over 10 functions) for a future day using three predictive approaches. The results are averaged over 4 clusters of patients as described in 220.

Figure 17:
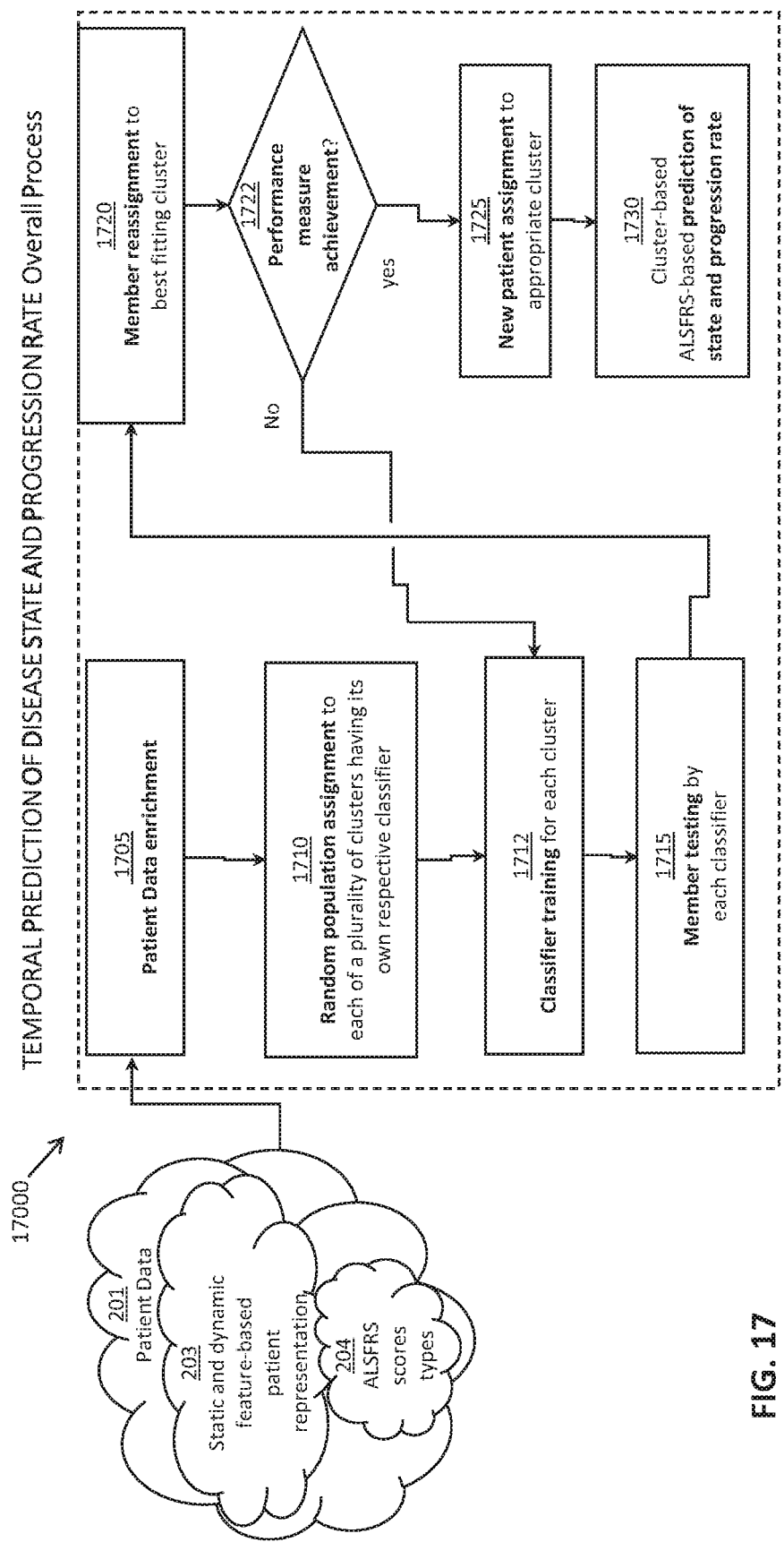
FIG. 17 depicts a flow chart employed by a second embodiment of the integrated system implemented for temporal prediction of disease state.

FIG. 17 depicts a flow chart employed by a second embodiment of integrated system 100 configured to implement a prediction-based stratification.

Specifically, in step 1705 patient data 201 is rendered into static and dynamic feature-based patient representation 203.

As noted before, the PRO-ACT database includes longitudinal data of ALS patients. The input data for our algorithm (Table 9) include static variables, i.e., variables that do not change through time such as onset site and gender, as well as temporal variables such as forced vital capacity (FVC), and five laboratory test results, which were chosen based on their contribution for prediction. Only patients with no missing data have been used, 2,850 of them were used for training and 1,126 for testing, each with two to thirteen documented visits.

TABLE 9

An example for the input data variables for a specific patient. For simplicity, units of laboratory test results are not specified.

| | | Static variables | | Temporal variables | | | | |
|---|---|---|---|---|---|---|---|---|
| | | | | Days | | | | |
| ID | Visit's No. | Onset site | ... Gender | from diagnosis | Total ALSFRS | CK | ... | PVC |
| 4390 | 1 | Bulbar ... | Male | 0 | 35 | 405 | ... | 81 |
| 4390 | 2 | Bulbar ... | Male | 34 | 33 | 486 | ... | 79 |
| ... | ... | ... ... | ... | ... | ... | ... | ... | ... |
| 4390 | 12 | Bulbar ... | Male | 552 | 25 | 1096 | ... | 51 |

In this embodiment, ALS disease-state prediction is implemented through an LSTM-based network in which the target variable is the total sum of the ten ALSFRS functionality items (i.e., an integer in the range 0-40).

The network includes two layers of LSTM, with 200 hidden units each. The output of the second LSTM layer is the input of a neural network layer with 200 hidden units, which yields the system output.

This methodology advantageously extends previous conventionally methodologies for ALS disease state prediction that use the first three months in a patient record for training, and the one-year ALSFRS value as the target. Instead of using patient representation based on only a single observation using specific past visits to predict disease state in a specific future visit, we created multiple observations, each referring to a prediction of a different future visit, using different past visits, and thereby extended the research question of previous studies to that of prediction for multiple time periods.

Figure 18:
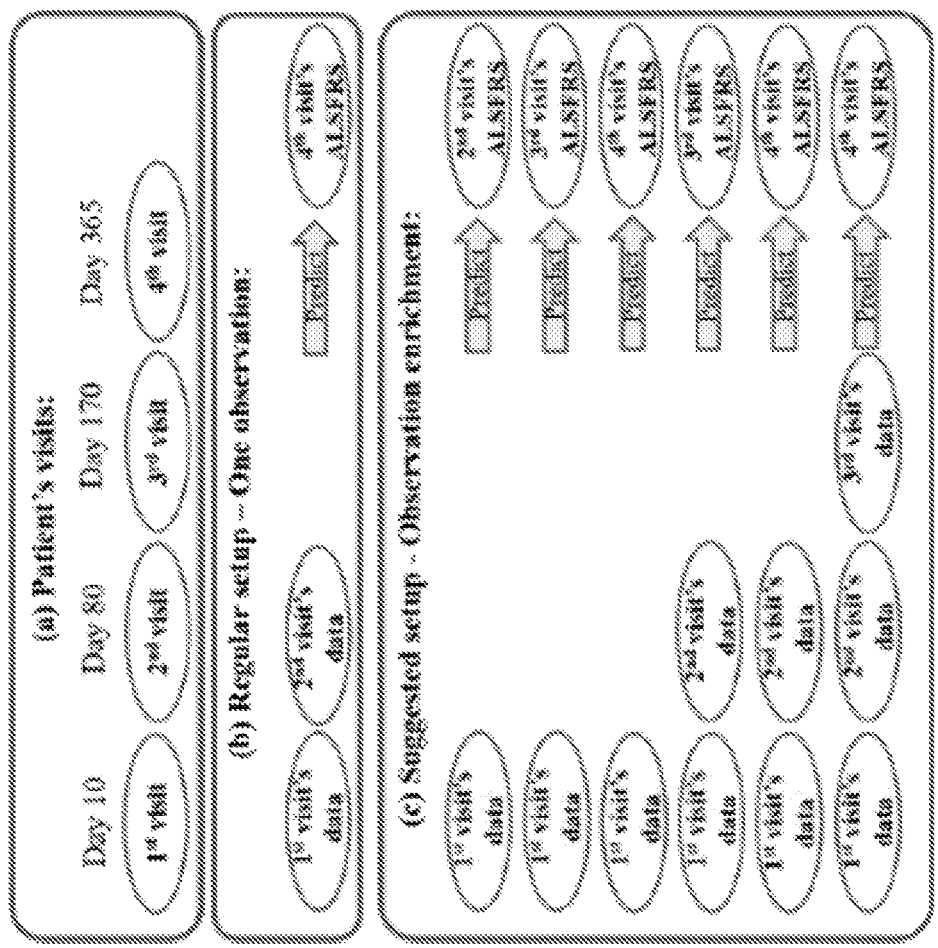
FIG. 18 depicts all documented visits for a sample patient, the training observation which is derived from the three-months to one-year prediction task, and a suggested enrichment methodology, respectively from top to bottom, in accordance with an embodiment.

FIG. 18 demonstrates the suggested enrichment method (step 1705 of FIG. 17): Display (a) presents all visits an example training patient has, whereas Display (b) demonstrates the previous methodology by which visit 3 (held on day 170 for this patient, after the three-month conventional training period has ended) does not contribute to the training and only a single observation represents this patient. The suggested enrichment methodology, shown in Display (c), makes six observations out of the patient record, allowing the model to use all data for this patient, and to learn a more flexible prediction model.

Algorithm 2 for clustering ALS patients is based on an iterative process intended to create in its termination K clusters each reflecting a different deterioration rate of the disease is shown below:

```
Algorithm 2

1:  procedure LSTM_CLUSTERING(temporal_data, K, P, Y)
2:      A_p ← random(1, K) for p ∈ {1, ..., P}
3:      r ← 1
4:      i ← 1
5:      while r > 0.05 do
6:          number_of_transitions ← 0
7:          for k in 1, ... K do * Training phase
8:              P_k ← {p|A_p = k}
9:              M_k ← train_LSTM(temporal_data, P_k, i)
10:         for p in 1, ..., P do * Reassignment phase
11:             for k in 1, ..., K do
12:                 Ŷ_{pMk} ← predict(temporal_data, M_k, p)
13:                 E_{pMk} ← |Ŷ_{pMk} − Y_p|
14:             if (argmin_k E_{pMk}) ≠ A_p then
15:                 number_of_transitions ++
16:             A_p ← argmin_k E_{pMk}
```

-continued

```
Algorithm 2

17:         r ← number_of_transitions / P
18:         i++
19:     return A, M
```

LSTM Clustering

Still with reference to FIG. 17, in step 1710, each patient in the population is randomly assigned to one of the K clusters. The number of clusters K is pre-specified by the user. At this point, the clusters do not reflect different deterioration rates, since they each have patients that resemble the whole ALS population, which is very heterogeneous, as presented before.

After the assignment, the iterative process is started in which in each iteration, we have a training phase and a reassignment phase. In step 1712, the training phase, for each cluster k, a matching LSTM based model is trained using the group of patients that are currently assigned to the cluster (function train LSTM in Algorithm 2). After training is over, there are K trained LSTM-based networks, one for each cluster. In step 1720, the reassignment phase is implemented. In this phase, for each patient in the population, a prediction is made using three-months of data for predicting the ALSFRS value of the one-year clinic visit (function predict). The prediction is made K times, once by each cluster's LSTM model. An estimate of the absolute error is made for the K predictions. Patients having a model that has a lower error than the current patient's cluster's model, will be reassigned to the cluster whose model has the minimal error. This iterative process is repeated until less than 5% of the patients are reassigned. Using the LSTM-based prediction model, one is able to incorporate the fully longitudinal data in the clustering process. An important part of the algorithm is increasing the number of epochs in each iteration when training the LSTM-based models, starting from one epoch at the first iteration. Using initially a small number of epochs is intended for underfitting to the training data of each cluster in the first iterations. Underfitting ensures the model does not adjust its weight to fit all patients that are assigned to the cluster; but only to the dominant group of patients in the cluster, i.e., the largest group of patients with a similar deterioration rate within the cluster. In different clusters, different deterioration rates will be represented by the dominant group. Using this technique, the dominant group, which had the largest effect on the network's weights in each cluster, will stay in the cluster, while other patients will be reassigned to other clusters, thanks to the underfitting. The number of epochs is increased in each iteration, so that gradually the rate of patients who belong to the dominant group in the cluster increases, thereby reducing overfitting to undesired patients.

Figure 19A:
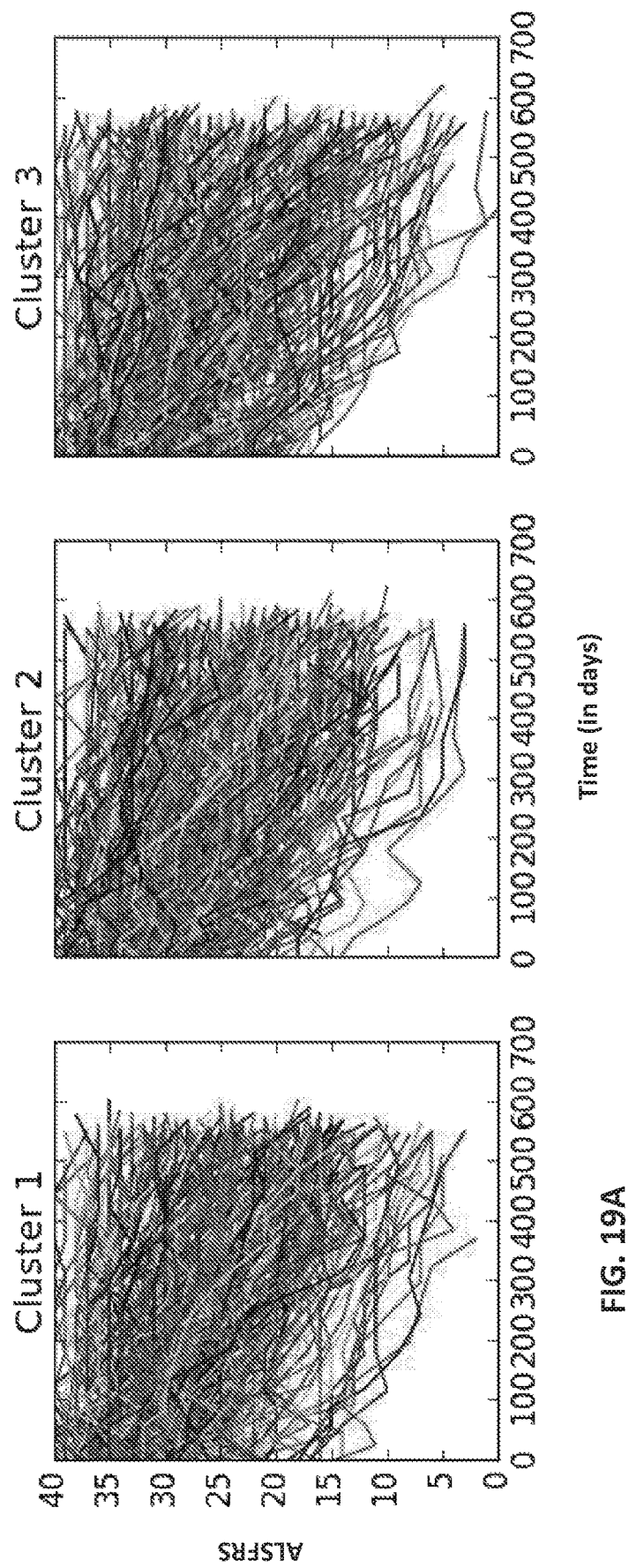
FIGS. 19A-19B are plots of ALSFRS trajectories of patients of three specific clusters for random initial population assignment and after member reassignment based on cluster-based classifiers, respectively, in accordance with an embodiment.
Figure 19B:
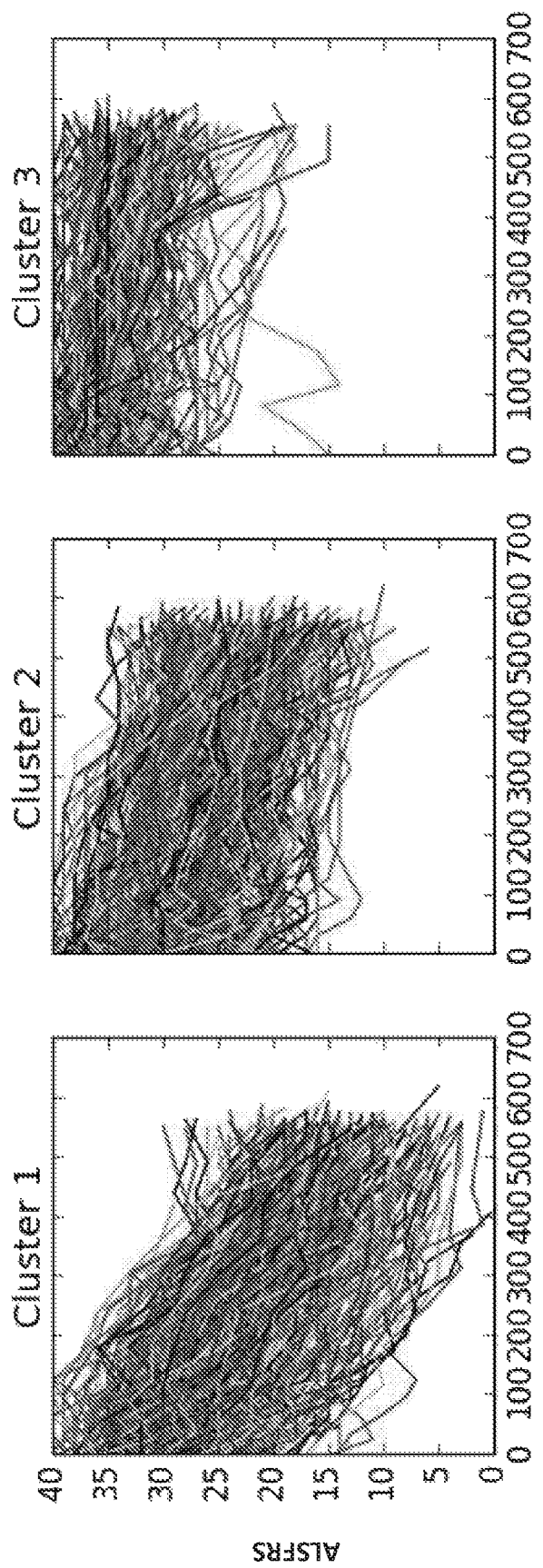

FIGS. 19A-19B present the initial and final assignment of patients to the three clusters. Each plot shows the trajectories of the ALSFRS of patients in the same cluster through time. In FIG. 19A, as can be seen, the randomly assigned clusters do not differ in the deterioration rates they represent. This fact justifies the low number of epochs; If their number were large, the LSTM model of each cluster would fit to all patients, and the reassigning process would hardly happen, not allowing the reception of clusters with different deterioration rates. The rate of patients who switched a cluster after the first iteration was around 65%. The rate kept decreasing from iteration to iteration. FIG. 19B presents the final assignment of the patients, when the algorithm reached convergence after ten iterations. The algorithm was able to create a meaningful subtyping of the patients; each cluster represents a different deterioration rate, as we wished. We ran the experiment ten times with different parts of the data using a 10-fold setup, and at all times, we received a similar clustering scheme.

Figure 20:
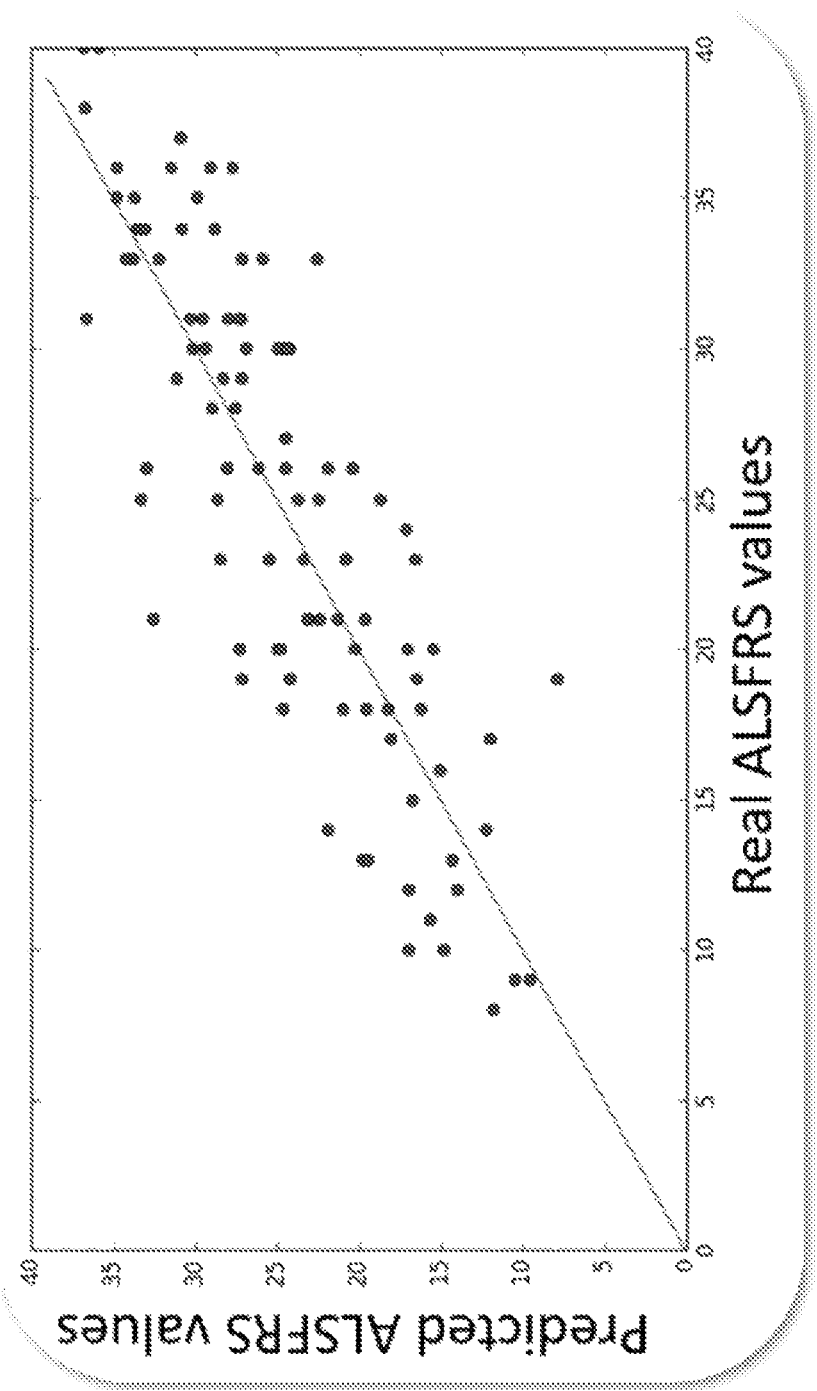
FIG. 20 compares ALSFRS predicted vs. real values for an LSTM-based model in a three-month to one-year prediction scenario, in accordance with an embodiment.

FIG. 20 compares ALSFRS predicted vs. real values for an LSTM-based model in a three-month to one-year prediction scenario. The predictions are close to the real values and are not clustered in a certain area in the graph, meaning that the model is not trying to reduce its error by making predictions based on common values in the data.

Now the task of individualized disease-state prediction based on the clustering scheme is examined. In order to make the prediction, first one needs, in step 1725, to assign the specific new patient to one of the clusters. Then in step 1730, one can use the cluster's LSTM model to make the prediction. The assignment of the patient is done based on predictions of a single LSTM model, i.e, one LSTM model which was trained using the data of all training patients (without clustering). For each patient, a first prediction is made using the single model, which has a good level of accuracy, as presented in FIG. 21. Then, K predictions are made using the model of each cluster. Out of the K predictions, the prediction that is the closest to the single model prediction is chosen. By that, the single model is used which already gave relatively good results, as a reference for making the cluster assignment, with the hope of improving the prediction results.

FIGS. 21A-21B present the predictions for two arbitrary patients, in the 180 and 39 day, respectively, which were produced by the single model vs. the prediction which were produced by the models of the two most likely clusters. In FIG. 21A, it is shown how when assigning the patient to a cluster that suits him most likely, it was possible to make a much more accurate prediction than the single model's prediction. In FIG. 21B, neither the single model nor the most likely cluster's model produced the most accurate prediction. It is shown that the second most likely cluster was the most accurate, showing another advantage of our model over the single model; using the single model, a point prediction is given for each future time point and the prediction cannot be further investigated, while with the clustering algorithm, there are several predictions each with a different likelihood enabling focus on the most likely prediction while considering less likely predictions and different possible trajectories. This capability is important in real-world applications. For example, when a physician gives an individualized Temporal (longitudinal) data (lab/imaging test results, patient functionality along the disease . . . ), and Manipulated data (manipulation of temporal data to account for time without using all temporal data as is, e.g., rate of disease deterioration between two time points).

Table 10 presents result comparison of the LSTM-based model with a state of-the-art prediction model, random forest (RF). RF is not a temporal model, but it was widely used in previous ALS machine learning competition and research. Three measures were used for evaluating the models' performance: (1) Root mean square error (RMSE), (2) Pearson's correlation coefficient 1 (PCC), and (3) Concordance index (CI). The values in the table are the mean results of a 10-fold CV experiment. The LSTM-based model outperformed the RF model in all measures. All differences are significant (with a p-value lower than 0.001).

TABLE 10

Model comparison.
Bold values represent outperformance.

| Model | RMSE | PCC | CI |
| --- | --- | --- | --- |
| LSTM | 4.202 | 0.742 | 0.724 |
| RF | 4.488 | 0.720 | 0.715 |

Figure 22A:
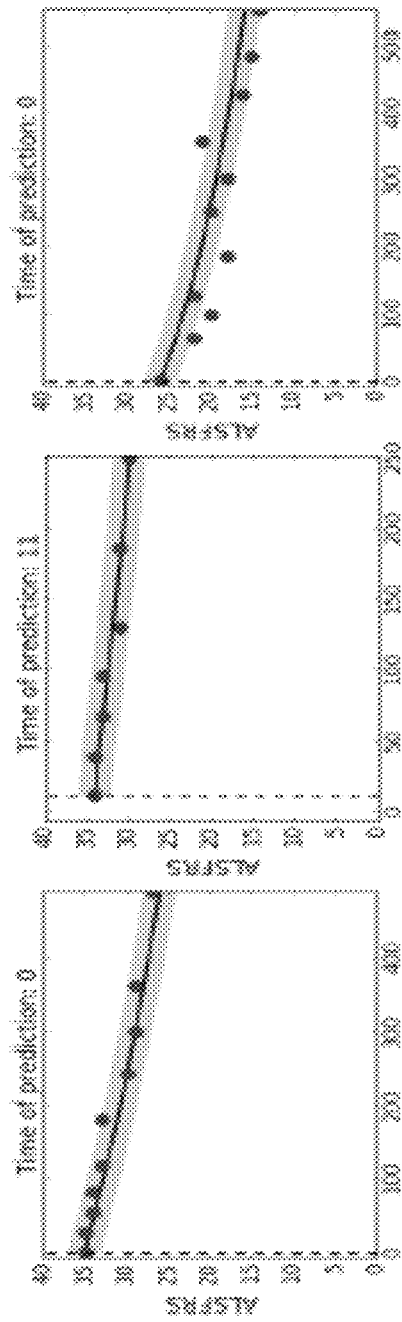
FIGS. 22A-22B depicts predictions of the disease trajectory as a function of the time of prediction in days in comparison to real ALSFRS values for three arbitrary more readily predictable patients and a single less predictable patient, respectively, according to an embodiment. It should be noted that figure titles are also embodiments in accordance with the above section.
Figure 22B:
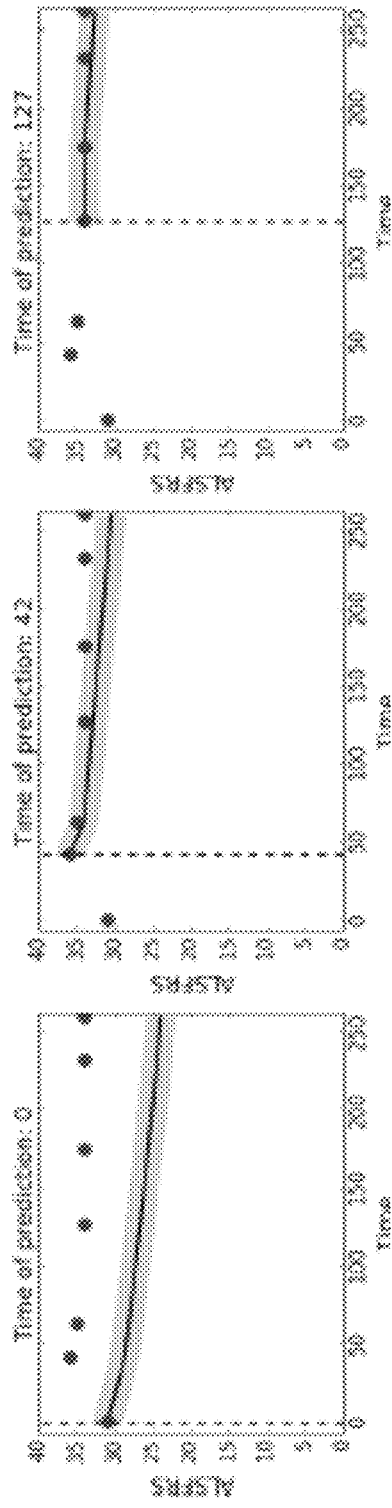

Specifically, the LSTM-based model can be used for individualized short-term (days or tens of days) and long-term (hundreds of days) predictions, due to our enrichment methodology. FIG. 22A shows the model's predictions for three arbitrary patients using only data of the first visit of each patient. In these cases, the model is able to make accurate short-term and long term predictions. Not in all cases were predictions accurate starting from the first visit, but due to the temporal nature of the model, predictions can be improved as more data regarding a patient are available. FIG. 22B demonstrates an online prediction for another arbitrary patient. In the first visit (in day 0), the predictions were not accurate. As more data were available, starting from visit 2 (in day 42) and continuing from visit 4 (in day 127), the model was able to improve the predictions. This example illustrates a great advantage of temporal modeling since the model is able to be adjusted in real time.

FIGS. 22A-22B depict prediction of the disease trajectory for four arbitrary patients from the test set. Red dots are real ALSFRS observations, the black line is the predicted trajectory, and the blue band is an interval representing a deviation of 5% of the maximum value (of 40) of the ALSFRS. The vertical dashed line corresponds to the time of prediction in days (detailed in the graph title), such that any observation made after the line was unavailable to the model at prediction time.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for predicting a disease state and/or progression rate performed on a computing device having a processor, memory, and one or more code sets stored in the memory and executed in the processor, the method comprising:
    receiving feature-based representations of a first plurality of patients, the feature-based representations including static and dynamic features;
    assigning a second plurality of plurality of patients among a plurality of patient clusters, each of the plurality of second patients represented with said static and dynamic features;
    training a cluster-specific classifier for each of the plurality of patient clusters, each respective cluster-specific classifier operative to predict a disease state for a portion of the second plurality of patients of a respective one of the plurality of patient clusters;
    iteratively running a training cycle until a performance measure is achieved, the training cycle including:
        predicting disease states for the portion of the second plurality of patients with each of the respective cluster-specific classifiers,
        reassigning at least one of the plurality of second patients to a different one of the plurality of patient clusters, wherein the respective cluster-specific classifier of the different patient cluster predicts a disease state and/or progression rate best matching a true disease state and/or a progression rate of said at least one of the plurality of second patients, and
        retraining each of the respective cluster-specific classifiers using patients associated with each of the plurality of patient clusters after the reassigning;
    receiving feature-based representations of a new patient;
    assigning the new patient to a particular one of the plurality of patient clusters based on the received feature-based representations of the new patient; and
    using the retrained cluster-specific classifier of the particular patient cluster to predict a disease state and/or progression rate of the new patient.

2. The method of claim 1, wherein said receiving the feature-based representations of the first plurality of patients comprises receiving a plurality of observed features for each of the plurality of first patients; and
    wherein said feature-based patient representations for each said of the plurality of first patients is based on a combinatorial combination of said observed features.

3. The method of claim 1, assigning said new patient to the particular patient cluster in accordance with a cluster-specific prediction most closely matching an approximate disease state and/or approximate progression rate determined using a general non-cluster prediction model.

4. The method according to claim 3, comprising training said general non-cluster prediction model using said received feature-based representation of patients; wherein said assigning of said new patient comprises:
    predicting an approximate disease state and/or approximate progression rate for said new patient using said general non-cluster prediction model;
    predicting a plurality of cluster-specific disease states and/or cluster-specific progression rates for said new patient, a cluster-specific disease state and/or cluster-specific progression rate predicted using each of the respective cluster-specific classifiers; and
    assigning said new patient to a cluster a cluster-specific disease state and/or cluster-specific progression rate best matches said approximate disease state and/or approximate progression rate;
    outputting said disease state or and/progression rate predicted by said assigned cluster-specific classifier for said new patient.

5. The method according to claim 1, wherein said receiving the feature-based representations of the first plurality of patients comprises receiving feature-based representations of neurodegenerative disease (ND) patients; and
    wherein said disease state and/or progression rate are characterized by Functionality Measure (FM) items and/or their change.

6. The method according to claim 1, wherein said dynamic features include multiple values over time.

7. The method according to claim 1, wherein said performance measure is reached when less than a selected percentage of said second plurality of patients are reassigned.

8. The method according to claim 7, wherein said percentage is 5%.

9. The method according to claim 1, wherein said training is intended for underfitting the training data of each of the plurality of patient clusters to provide a cluster-specific classifier which only fits a dominant group of patients in the each said patient cluster; and
    wherein said iteratively running comprises decreasing underfitting of said retraining with each iteration.

10. The method according to claim 9, wherein said training starts using one epoch; and
    wherein said iteratively running comprises increasing a number of epochs with each iteration.

11. The method according to claim 1, comprising receiving a pre-specified number of the plurality of patient clusters; and
    wherein said assigning is among said number of the plurality of patient clusters.

12. The method according to claim 1, wherein said predicting a disease state and/or progression rate includes providing a predicted disease state and/or progression rate at a future time.

13. The method according to claim 1, wherein at least one of said cluster-specific classifiers is a temporal modelling based classifier.

14. The method according to claim 13, wherein at least one of said cluster-specific classifiers is a long short-term memory (LSTM)-based cluster-specific classifier.

15. The method according to claim 1, wherein said assigning comprises randomly assigning said second plurality of patients among said plurality of patient clusters.

16. The method according to claim 1, wherein said assigning the second plurality of patients comprises, for said feature-based representations of patients:
    calculating progression rates for individual features of said feature-based representations of patients;
    for each of said second plurality of patients, establishing a multi-dimensional patient representation based on the feature progression rates to provide a plurality of multi-dimensional patient representations; and clustering the plurality of multi-dimensional patient representations into a plurality of patient clusters.

17. The method according to claim 16, wherein said establishing said multi-dimensional patient representation comprises:
grouping individual features into body function groups; and
calculating body function group progression rates for each of the body function groups.

18. A system for predicting a disease state and/or progression rate, the system comprising:
an input device operative to receive feature-based representation of a first plurality of patients, the feature-based representation including static and dynamic features;
a computing device configured to:
assign a second plurality of plurality of patients among a plurality of patient clusters, each of the plurality of second patients represented with said static and dynamic features,
train a cluster-specific classifier for each of the plurality of patient clusters, each respective cluster-specific classifier operative to predict a disease state for a portion of the second plurality of patients of a respective one of the plurality of associated patient clusters;
iteratively run a training cycle until a performance measure is achieved, the training cycle including:
predicting disease states for the portion of the second plurality of patients with each of the respective cluster-specific classifiers,
reassigning at least one of the plurality of second patients to a different one of the plurality of patient clusters, wherein the respective cluster-specific classifier of the different patient cluster predicts a disease state and/or progression rate best matching a true disease state and/or a progression rate of said at least one of the plurality of second patients, and
retraining each of the respective cluster-specific classifiers using patients associated with each of the plurality of patient clusters after the reassigning;
receive feature-based representations of a new patient;
assign the new patient to a particular one of the plurality of patient clusters based on the received feature-based representations of the new patient; and
use the retrained cluster-specific classifier of the particular patient cluster to predict a disease state and/or progression rate of the new patient; and
an output device operative to output the disease state and/or progression rate.

19. The system of claim 18, wherein said input device is operative to receive a plurality of observed features for each of the plurality of first patients; and
wherein the feature-based patient representation for each of the plurality of first patients is based on a combinatorial combination of previously observed features.

20. The system of claim 18, wherein the computing device is configured to assign said new patient to the particular patient cluster in accordance with a cluster-specific prediction most closely matching an approximate disease state and/or approximate progression rate determined using a general non-cluster prediction model.

* * * * *